(12) United States Patent
Sun

(10) Patent No.: US 11,786,384 B2
(45) Date of Patent: Oct. 17, 2023

(54) ASSISTANCE DEVICE AND CONTROL METHOD THEREFOR

(71) Applicant: BIONICM INC., Tokyo (JP)

(72) Inventor: Xiaojun Sun, Tokyo (JP)

(73) Assignee: BIONICM INC., Tokyo (JP)

( * ) Notice: Subject to any disclaimer, the term of this patent is extended or adjusted under 35 U.S.C. 154(b) by 163 days.

(21) Appl. No.: 16/980,690

(22) PCT Filed: Mar. 13, 2019

(86) PCT No.: PCT/JP2019/010274
§ 371 (c)(1),
(2) Date: Sep. 14, 2020

(87) PCT Pub. No.: WO2019/177022
PCT Pub. Date: Sep. 19, 2019

(65) Prior Publication Data
US 2021/0015637 A1 Jan. 21, 2021

(30) Foreign Application Priority Data
Mar. 13, 2018 (JP) .................................. 2018-045451

(51) Int. Cl.
*A61F 2/66* (2006.01)
*A61F 2/70* (2006.01)
(Continued)

(52) U.S. Cl.
CPC .............. *A61F 2/6607* (2013.01); *A61F 2/70* (2013.01); *A61F 2/76* (2013.01);
(Continued)

(58) Field of Classification Search
CPC .. A61F 2/6607; A61F 2/70; A61F 2/76; A61F 2002/5072; A61F 2002/607;
(Continued)

(56) References Cited

U.S. PATENT DOCUMENTS 11,123,171 B2 * 9/2021 Forsell .................. A61F 2/0036
2007/0050044 A1 3/2007 Haynes et al.
(Continued)

FOREIGN PATENT DOCUMENTS

JP 200754086 A 3/2007
JP 2017-388 A 1/2017
(Continued)

OTHER PUBLICATIONS

Bionx, Instructions for Use BiOM T2 Ankle, (2013), pp. 7,34,35 (Year: 2013).*

(Continued)

*Primary Examiner* — Keri J Nelson
*Assistant Examiner* — Aren Patel
(74) *Attorney, Agent, or Firm* — Hayes Soloway PC

(57) ABSTRACT

An assistance device is described to assist a joint motion of a lower limb. The assistance device includes a driving part, an elastic part, and a crank mechanism. The driving part includes a motor and a transmission mechanism to change a speed of the motor and converts a rotational motion of the motor into a linear motion. The elastic part includes at least: a series spring provided in series between the transmission mechanism and the crank mechanism, a first parallel spring provided between the driving part and the ankle part, and a second parallel spring provided between the ankle part and the foot part. The crank mechanism is provided between the driving part and the foot part and converts the linear motion to a rotational motion while changing a deceleration coefficient according to an ankle angle.

11 Claims, 37 Drawing Sheets

(51) Int. Cl.
*A61F 2/76* (2006.01)
*A61F 2/50* (2006.01)
*A61F 2/60* (2006.01)

(52) U.S. Cl.
CPC . *A61F 2002/5072* (2013.01); *A61F 2002/607* (2013.01); *A61F 2002/6614* (2013.01); *A61F 2002/701* (2013.01); *A61F 2002/764* (2013.01); *A61F 2002/7645* (2013.01)

(58) Field of Classification Search
CPC ........ A61F 2002/6614; A61F 2002/701; A61F 2002/764; A61F 2002/7645
See application file for complete search history.

(56) References Cited

U.S. PATENT DOCUMENTS

| | | | |
|---|---|---|---|
| 2007/0050047 A1 | 3/2007 | Ragnarsdottlr et al. | |
| 2013/0024006 A1 | 1/2013 | Balli et al. | |
| 2013/0274894 A1* | 10/2013 | Goldfarb | A61F 2/70 623/24 |
| 2013/0310949 A1* | 11/2013 | Goldfarb | A61F 2/70 623/27 |
| 2016/0158029 A1 | 6/2016 | Kuiken et al. | |
| 2017/0290684 A1* | 10/2017 | Lenzi | A61F 2/70 |
| 2019/0175365 A1* | 6/2019 | Herr | A61F 2/68 |

FOREIGN PATENT DOCUMENTS

| | | | | |
|---|---|---|---|---|
| KR | 10-2008-0075251 A | | 8/2008 | |
| KR | 10-2008-0075465 A | | 8/2008 | |
| KR | 20080075251 A | * | 8/2008 | ............... A61F 2/66 |
| WO | 2010027968 A2 | | 3/2010 | |
| WO | 2017094922 A1 | | 6/2017 | |

OTHER PUBLICATIONS

Michael Franco, "A bionic ankle so natural, it's worth a happy dance", Apr. 17, 2014, CNET, (Year: 2014).*

European Search Report dated Nov. 12, 2021 in copending European Application 19767689.3.

Taiwan Application No. 108108480, Filed Mar. 13, 2018, Office Action dated Jan. 10, 2019, English Translation.

* cited by examiner

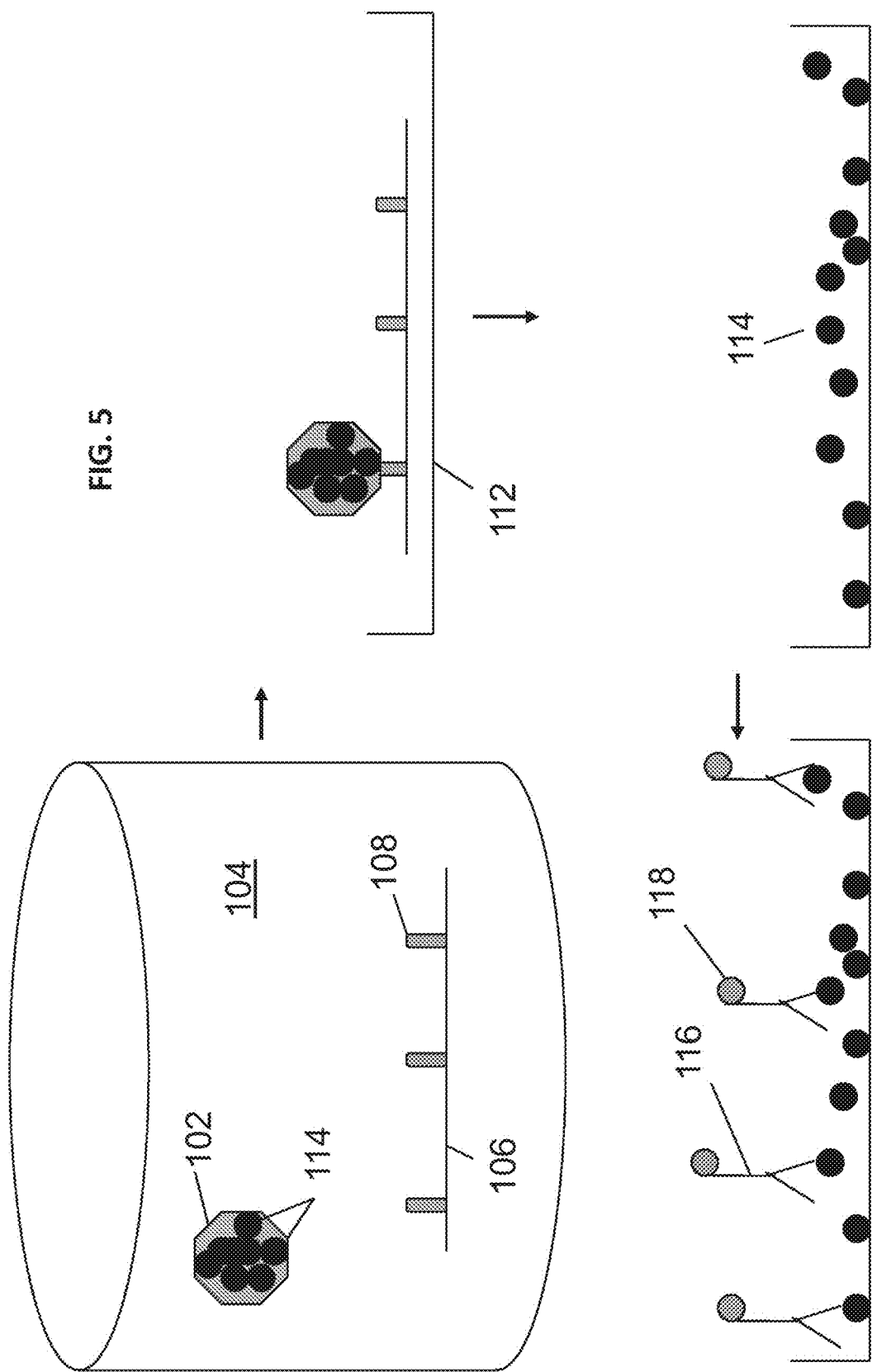

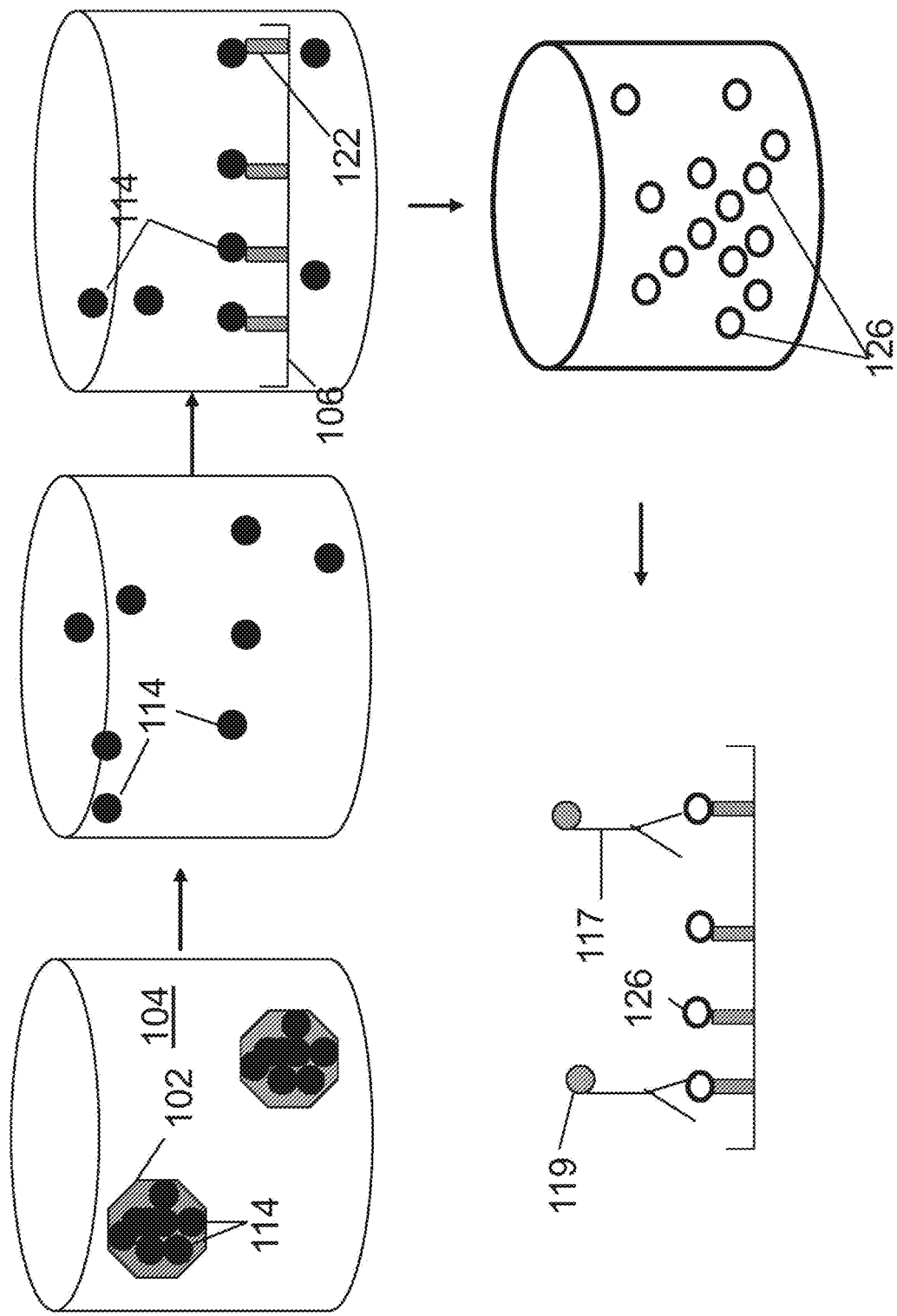

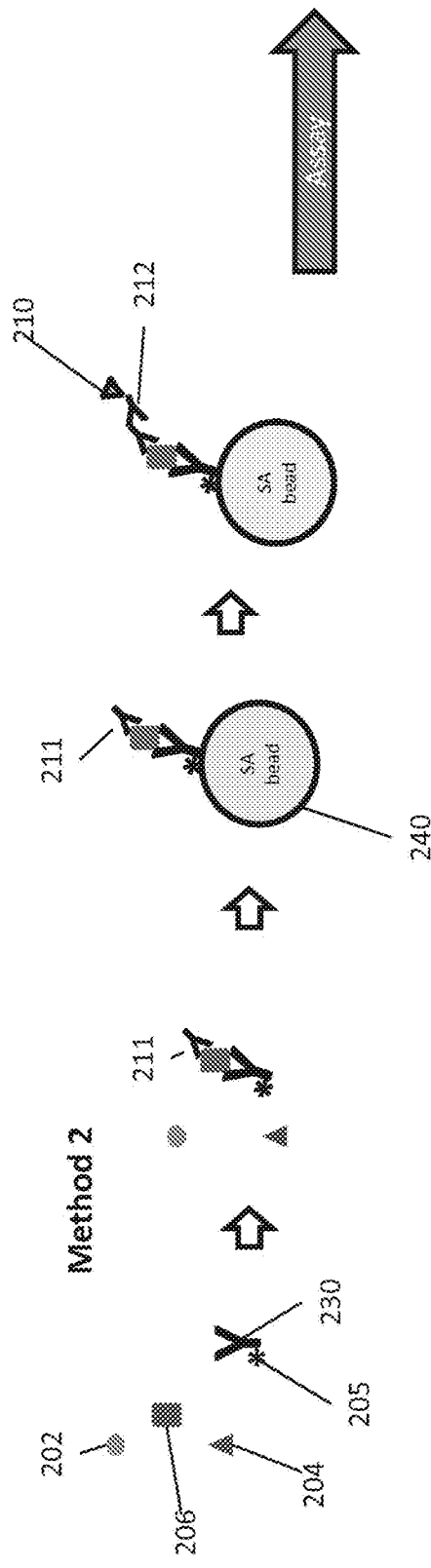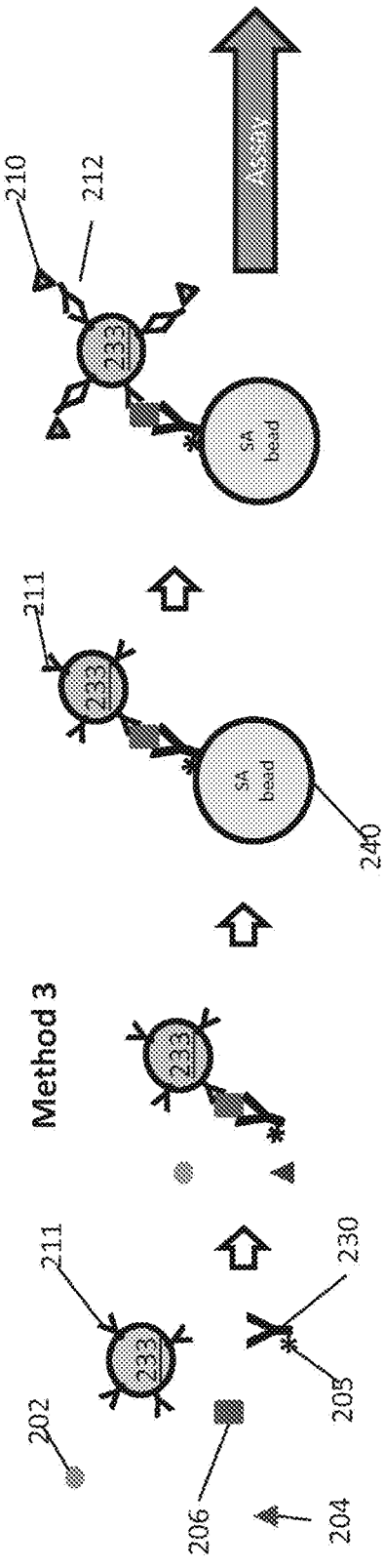

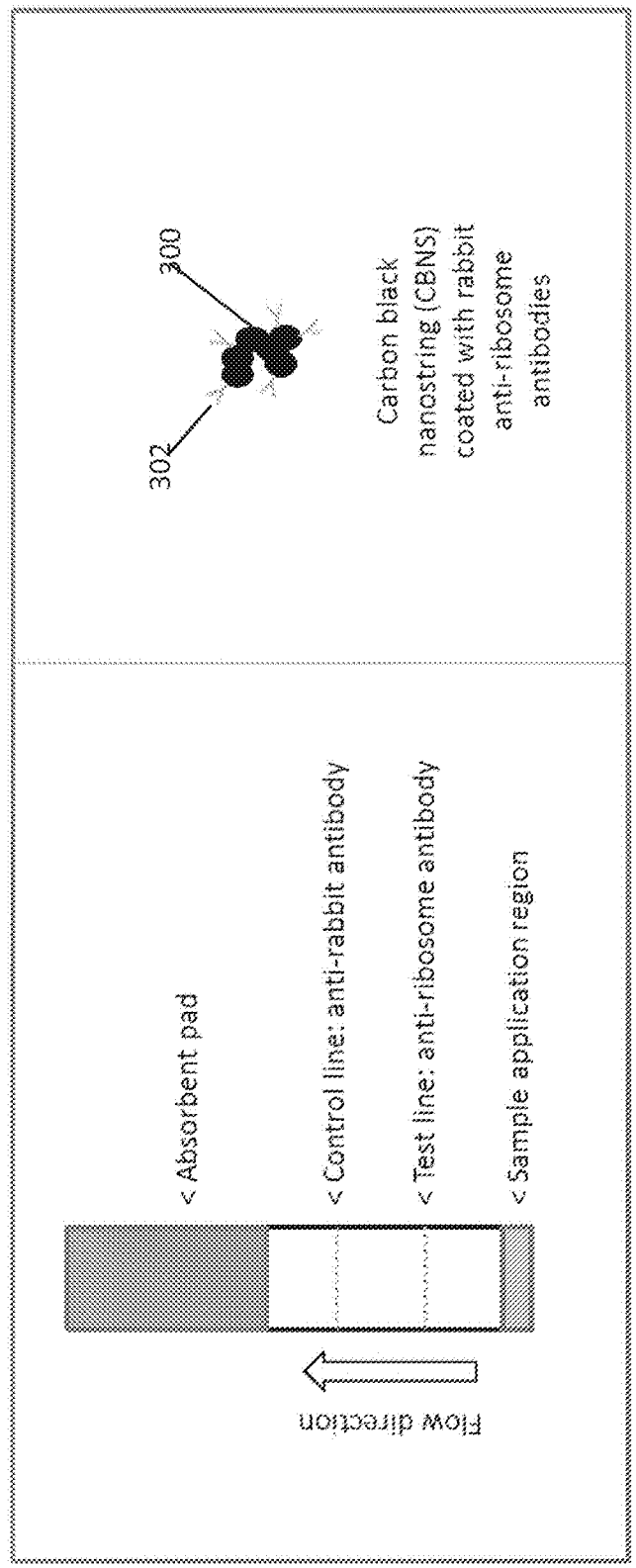

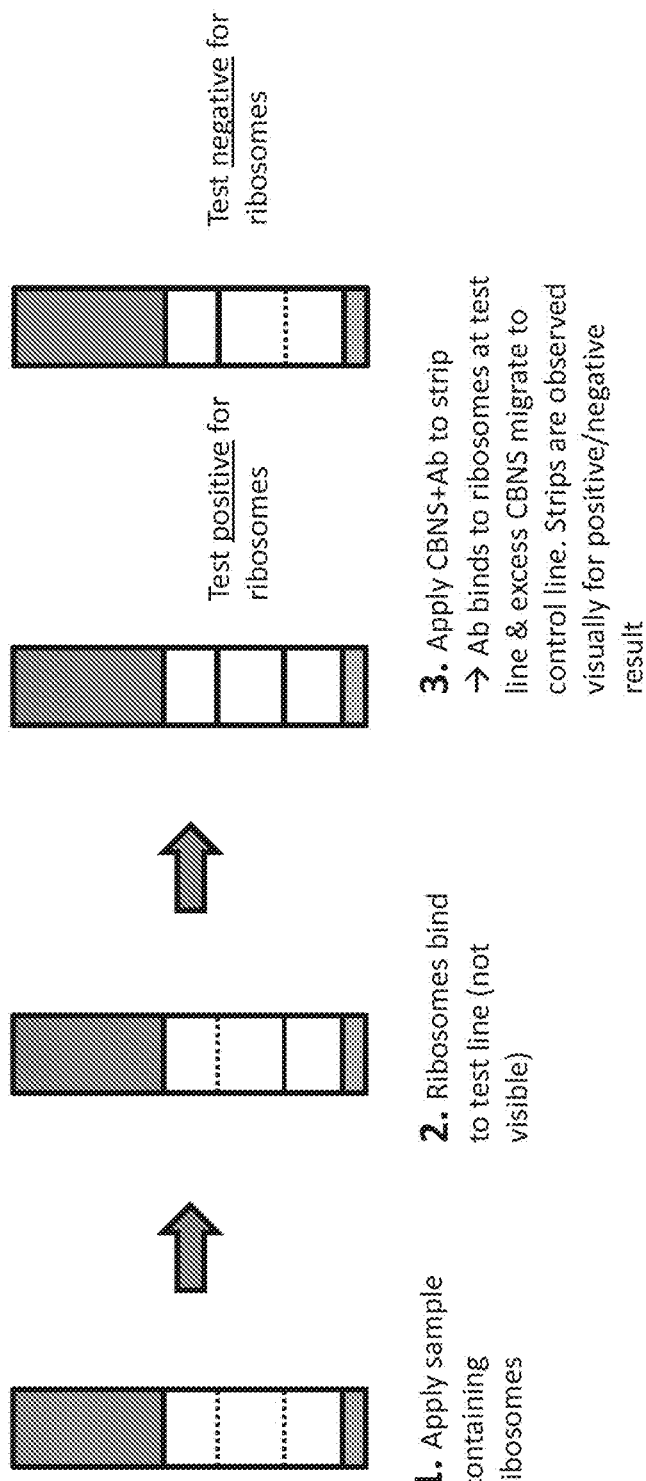

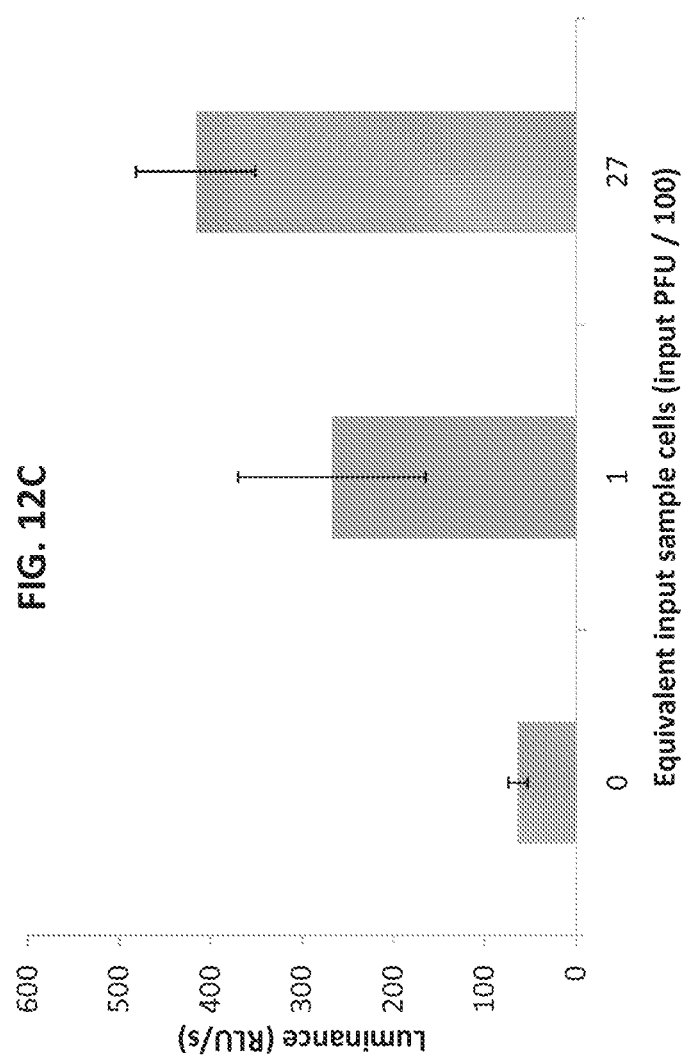

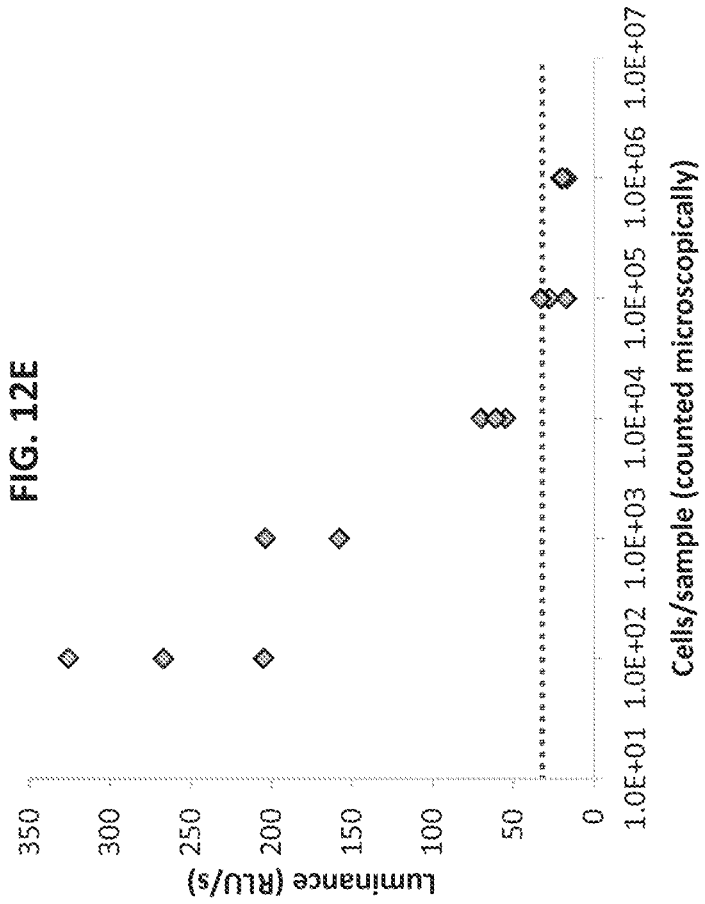

ASSISTANCE DEVICE AND CONTROL METHOD THEREFOR

CROSS-REFERENCE TO RELATED APPLICATIONS AND PRIORITY

This patent application claims priority from PCT Patent Application No. PCT/JP2019/010274 filed Mar. 13, 2019, which claims priority from JP Patent Application No. 2018-045451 filed Mar. 13, 2018. Each of these patent applications are herein incorporated by reference in its/their entirety.

TECHNICAL FIELD

The present invention relates to an assistance device and a control method thereof.

BACKGROUND

In an assistance device to assist joint motion of a limb, conventionally, three types of a passive type, an electronic control type and an active type are mainly adopted. Among them, the active type controls the extension and bending angles of the elbow, the knee and the ankle joint by using driving means such as a motor, thereby assisting movement of the joint in motions such as grasping and walking.

However, in the conventional active type assistance device, a large motor needs to be operated at all times in order to obtain a high driving torque at the end joint, and since energy efficiency is poor, a battery having a large capacity is required, and the device itself tends to become large in weight.

PRIOR ART REFERENCE

Patent Document

Patent Document 1: US patent application publication No. 2016/0158029
Patent Document 2: Korean patent application publication No. 10-2008-0075465

SUMMARY

Problems to Be Solved

The problem to be solved by the present invention is to provide an assistance device excellent in energy efficiency and a control method thereof.

Means for Solving the Problem

In order to solve the above problem, an assistance device according to one embodiment of the present invention is an assistance device which assists the motion of a joint of a lower limb, and includes: a driving part which includes a motor and a transmission mechanism to change the speed of the motor, and converts a rotational motion of the motor into a linear motion; an elastic part which alleviates an impact from an object through a foot part and accumulates an impact force or self-gravity by compression, and releases an accumulated energy by stretching to apply an energizing force for motion assistance; and a crank mechanism which is provided between the driving part and the foot part, and converts the linear motion to the rotational motion while changing a deceleration coefficient according to the ankle angle.

According to the assistance device of one embodiment of the present invention, since a crank mechanism which is provided between the driving part and the foot part and converts the linear motion into the rotational motion while changing the deceleration coefficient according to the ankle angle and transmits it to the foot, it is possible to mechanically realize the angle-torque relationship characteristics of a human ankle and electrically suppress energy consumption, thereby providing an assistance device having excellent energy efficiency through downsizing and weight reduction of the device.

Further, a control method of an assistance device according to another embodiment of the present invention is a control method of an assistance device to assist the joint motion of a lower limb. The assistance device includes: a driving part which includes a motor and a transmission mechanism to change a speed of the motor, and converts a rotational motion of the motor into a linear motion; an elastic part which alleviates an impact from an object through a foot part and accumulates an impact force by compression, and releases an accumulated impact force by stretching to apply an energizing force for motion assistance; and a crank mechanism which is provided between the driving part and the foot part, and converts the linear motion into a rotational motion while changing a deceleration coefficient according to the ankle angle. In this method, a torque of the motor is adjusted by estimating a moving situation of a user within a walking cycle and controlling the driving part according to the estimated moving situation.

According to the control method of the assistance device in accordance with the embodiment of the present invention, since the torque of the motor is adjusted by estimating the moving situation of the user within the walking cycle and controlling the driving part according to the estimated moving situation relationship, it is possible to assist walking by accumulating and releasing energy by the elastic part in addition to controlling the assistance device with excellent energy efficiency.

In this specification, the term "assist" is a concept including replacing, and is applied not only to a device such as an artificial hand or an artificial foot for replacing a part of a deficient limb, but also to a device such as a power suit for assisting movement of a joint. In addition, the term "ankle" includes not only ankle joints but also knee joints, hip joints, and the like.

BRIEF DESCRIPTION OF DRAWINGS

FIG. 5A is a perspective view showing a specific configuration of the assistance device according to the first embodiment of the present invention.
FIG. 5B is an example of a perspective view showing a specific configuration in a state where the frame is removed from the assistance device shown in FIG. 5A.

FIG. 6A is a cross-sectional view taken along the line A-A of FIG. 5A.

FIG. 6B is an example of a front view showing a specific configuration in a state where the frame is removed from the assistance device shown in FIG. 5A.

DETAILED DESCRIPTION

Figure 1A:
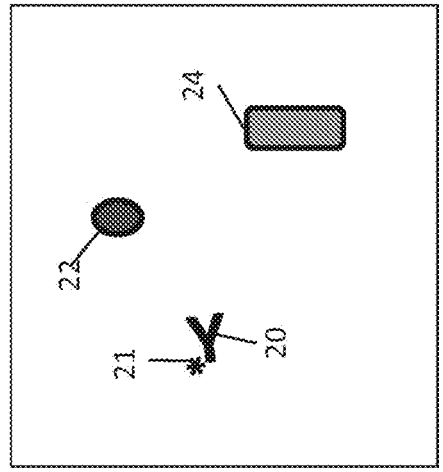
FIG. 1 is a schematic diagram showing a walking cycle of a person.
Figure 1B:
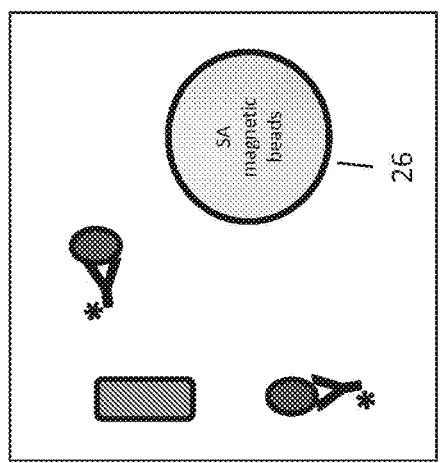
Figure 1C:
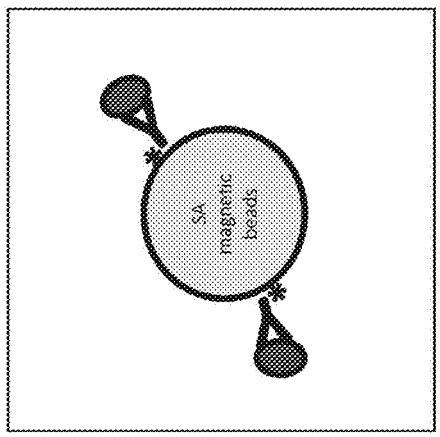
Figure 1D:
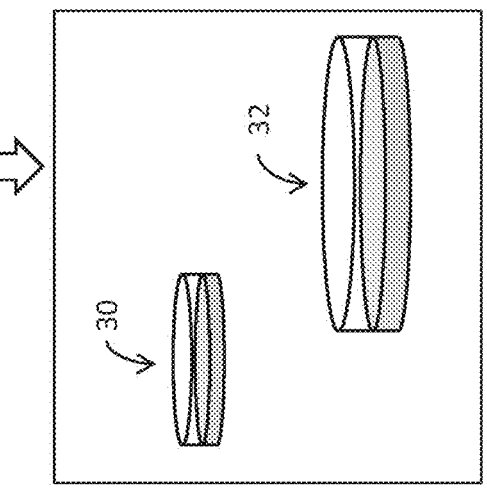
Figure 1E:
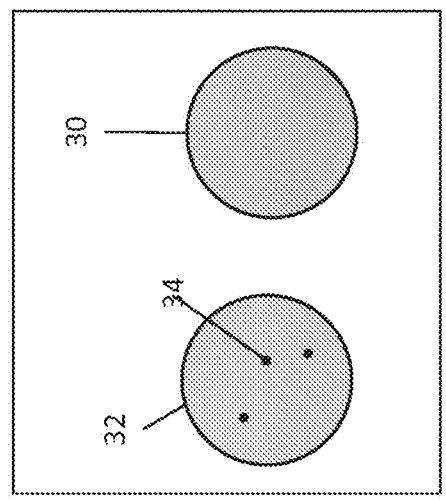

Hereinafter, some of the embodiments will be described with reference to the drawings. In the drawings, the same parts are designated by the same reference numerals, and duplicate description thereof will be omitted as appropriate. It should be noted that the accompanying drawings are illustrated for the description of the invention and for facilitating understanding thereof, and that the shapes, dimensions, ratios, etc. in each drawing are different from the actual device.

Further, the terms indicating directions such as up and down in the description indicate relative directions when the socket described later is arranged so as to be located above the foot part. Therefore, it may be different from the actual direction based on the gravitational acceleration direction.

Hereinafter, a case where the assistance device according to the present invention is applied to an artificial foot will be described as an example, but the present invention is not limited to this case, and can be applied to knee joints other than artificial foots, limbs other than legs, for example, artificial hands attached to upper limbs, and other power suits.

(1) First Embodiment

FIG. 1 is a schematic diagram showing a walking cycle of a person. As shown in the figure, the walking cycle of a person is composed of a stance phase and a swing phase. The stance phase refers to a period during which at least a part of the sole reaches the ground or the floor surface while walking and at least a part of the body weight is applied. The swing phase refers to a period from the time when the toes of the foot leave the ground or the floor surface during walking until the heel is next grounded, that is, a period during which the foot is swung away from the ground or the floor surface. It is to be noted that the floor surface is not limited to a horizontal one, but includes, for example, a step of a stairs with a change in height. In this specification, the ground or the floor surface corresponds to, for example, an "object".

As shown in the stance phase of FIG. 1, in the walking motion of a person, first, after the heel is grounded on the ground or the floor surface (1), the body weight moves forward from the heel to the foot tip (2), then the ground or the floor surface is kicked out from the toes (3), and finally the entire foot is separated from the ground or the floor surface (4).

Figure 2:
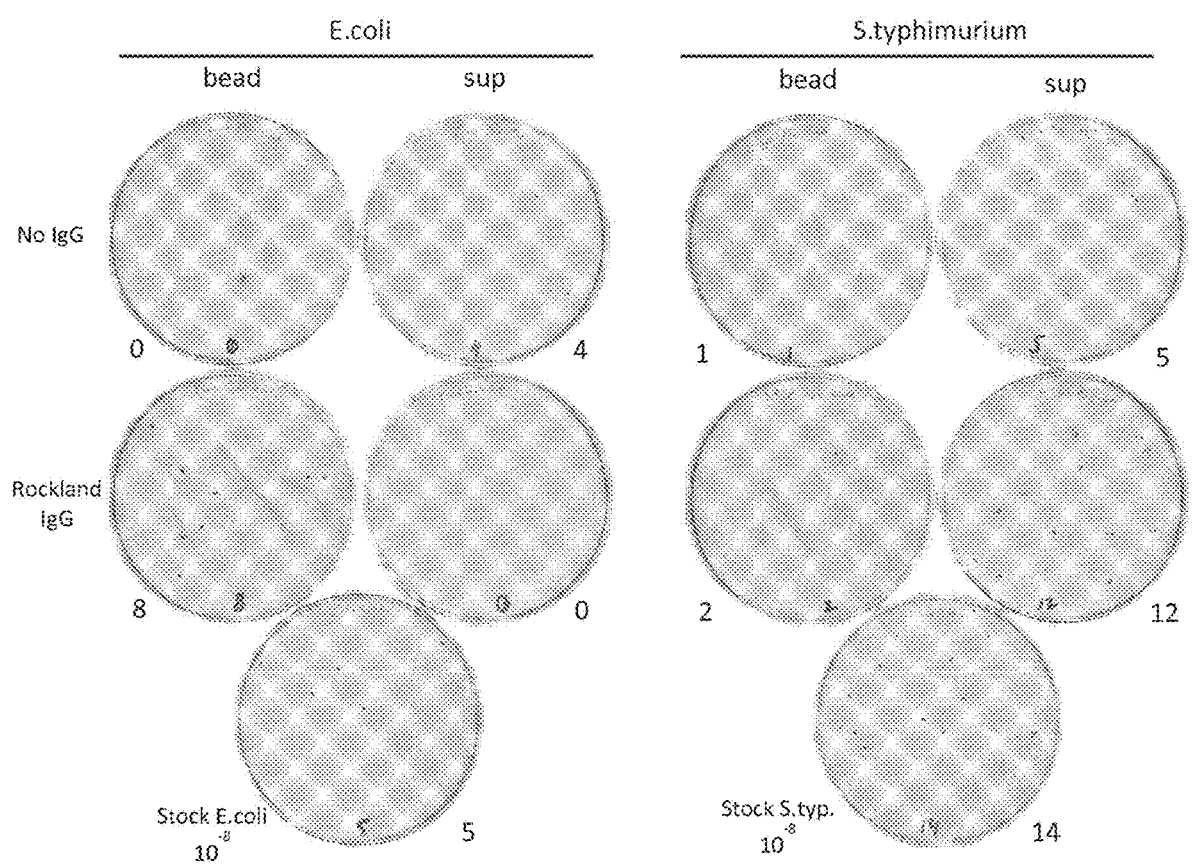
FIG. 2 is a diagram showing a relationship between ankle angle and plantar flexion/dorsal flexion.

FIG. 2 is a diagram showing a relationship between ankle angle and dorsal flexion/plantar flexion. A vertical direction, that is, a direction of 90° from the flat ground or the floor surface is taken as a reference, and bending of a foot tip toward the planta pedis (sole of the foot) than this reference direction is referred to as plantar flexion, and bending toward the dorsum pedis (instep of the foot) than this reference direction is referred to as dorsal flexion. In plantar flexion, the angle between the direction of the foot and the ground or the floor surface is less than 90°, and in dorsal flexion, the angle between the direction of the foot and the ground or the floor surface is greater than 90° (See FIG. 1).

Figure 3A:
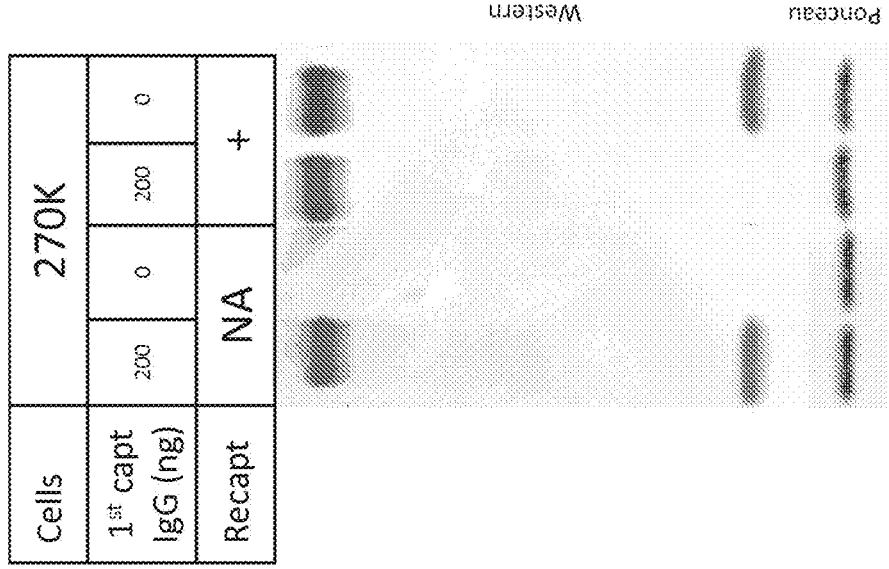
FIG. 3 is an example of a graph showing a relationship between an ankle angle and an ankle torque in a walking motion.
Figure 3B:
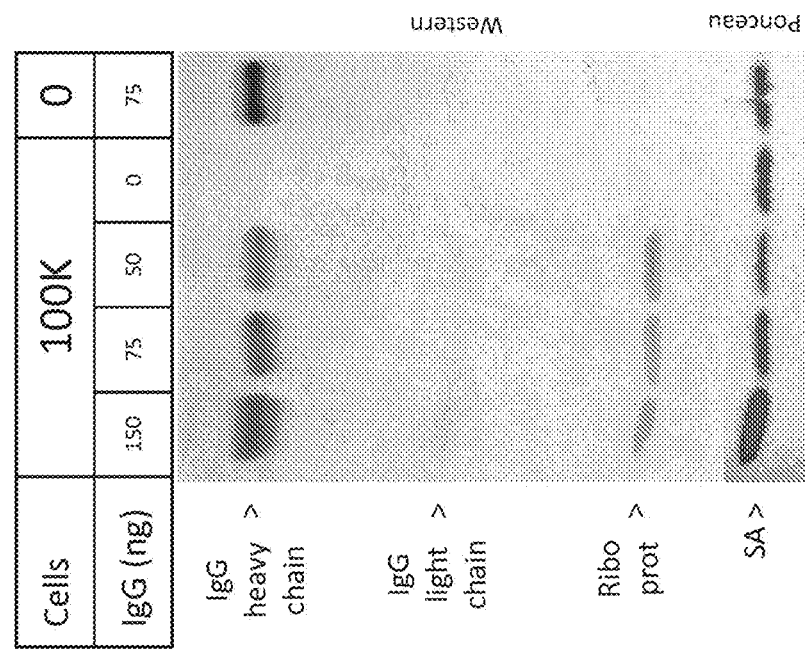

FIG. 3 is an example of a graph showing a relationship between an ankle angle and an ankle torque in a walking motion. Here, the ankle angle is defined as 0° (neutral) when it is perpendicular (i.e., forms an angle of 90° with the ground or the floor surface) to the ground or the floor surface on which the user walks. Therefore, when the ankle angle takes a positive value, dorsal flexion occurs, and when it takes a negative value, plantar flexion occurs. As shown in FIG. 3, the ankle torque is approximately zero from the heel is grounded (1) to the sole becomes flat (2), but the value (absolute value) of the ankle torque increases with the forward movement of the body weight due to the dorsal flexion ((2) to (3)), and after kicking out the ground or the floor surface (3), the ankle angle increases due to the plantar flexion and the value (absolute value) of the ankle torque decreases.

The person moves forward by kicking out the ground with the foot part immediately before the toes leave the ground or the floor surface. This operation is called push-off, and as shown in FIG. 3, a large amount of energy is required for push-off.

Figure 4A:
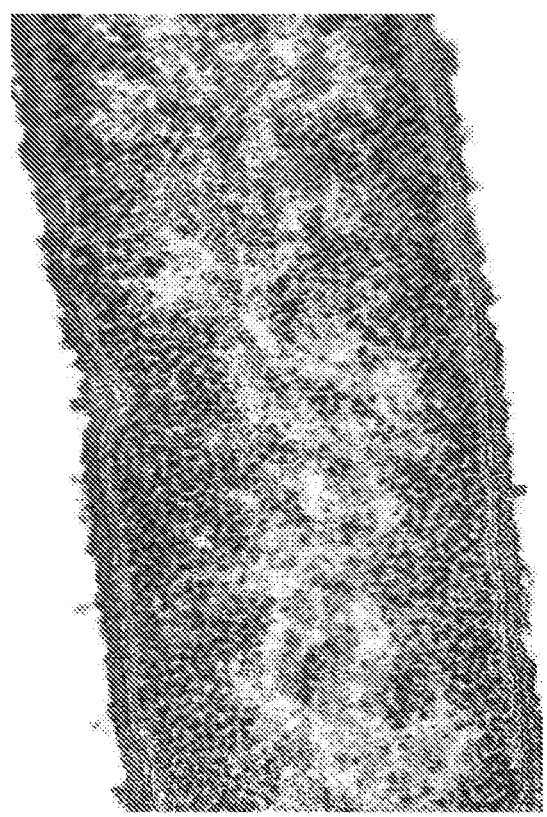
FIG. 4 is an example of a block diagram showing a main configuration of an assistance device according to the first embodiment of the present invention.
Figure 4B:
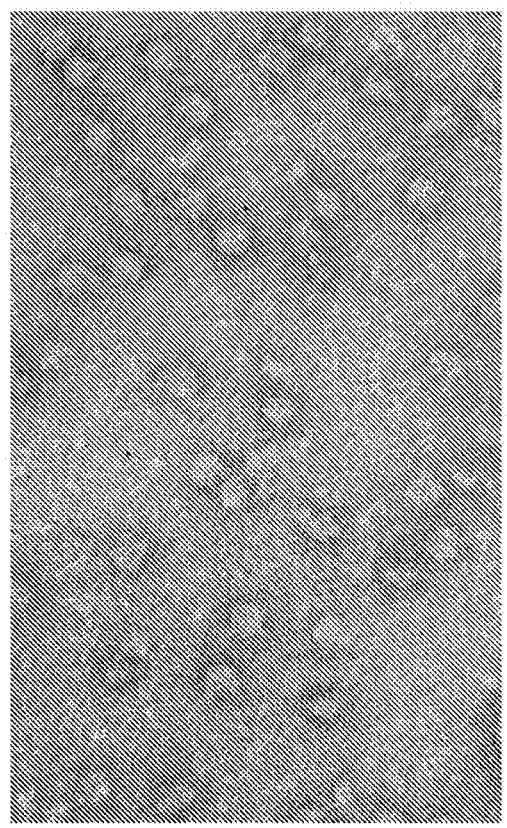

FIG. 4 is an example of a block diagram showing a main configuration of an assistance device according to the first embodiment of the present invention. The assistance device 1 according to the present embodiment includes a motor 10, a transmission mechanism 16, an elastic part 18, a slider crank 20, and an ankle part 24. The slider crank 20 includes a rod 22 and a crank 21. One end of the rod 22 is connected to the leading end of the cylinder 90 (see FIG. 7A) of the driving part, and the other end of the rod 22 is connected to one end of the crank 21. The cylinder 90 accommodates a ball nut 72, a plantar flexion spring 181 and a dorsal flexion spring 182 (see FIG. 7A). The cylinder 90 constitutes a linear motion unit together with its lid 92. The other end of the crank 21 is connected to a rotation shaft (not shown) of the ankle part 24. The other end on the side opposite to the linear motion unit side of the rod 22 makes circulation motion by the connection with the crank 21 by the linear (sliding) motion of the linear motion unit. Thereby, the crank 21 rotates around the rotation shaft (not shown) of the ankle part 24. As a result, the dorsal flexion/plantar flexion motion of the foot part 300 is performed. Of the both ends of the assistance device 1, the end on the motor 10 side is connected to a socket or knee prosthesis (not shown).

The motor 10 is connected to the battery 60 (see FIG. 8A) to perform a rotational motion. The motor 10 is connected to the ball screw 70 (see FIG. 6) via the transmission mechanism 16, whereby the rotational motion of the motor 10 is converted into rectilinear motion. The cylinder 90 accommodating the ball nut 72 of the ball screw 70 is connected to the slider crank 20, and its rectilinear motion is converted into rotational motion.

The ankle part 24 is connected to the crank 21 of the slider crank 20, whereby the rotational motion of the slider crank 20 is transmitted to the ankle part 24 to realize the advancement of the wearer by the foot part 300. The ankle part 24 corresponds to, for example, the "movable part" in this embodiment.

The elastic part 18 is arranged between the socket (not shown) and the slider crank 20, alleviates the impact when the foot part 300 lands on the ground or the floor surface and accumulates the impact force, and releases the accumulated impact force to apply an energizing force to the foot part 300 when the foot part 300 kicks out the ground or the floor surface.

The sensors SR1 to SR3 include an inertia measuring sensor SR1, an angle sensor SR2, and a force sensor SR3. The inertia measuring sensor SR1 detects the advancing speed of the assistance device 1 by detecting the angular velocity and acceleration of the assistance device 1. The angle sensor SR2 detects the ankle angle of the foot part 300. The force sensor SR3 detects the rotation (twist) of the rear surface of the foot part 300 by detecting the Y-axis moment of the foot part 300, in addition to detecting the magnitude of the force (repulsive force) from the ground or the floor surface caused by the body weight applied to the foot part 300 by the wearer. The sensors SR1 to SR3 are connected to a controller 50 and send respective detection signals to the controller 50.

The controller 50 is connected to the motor 10, the transmission mechanism 16 and the brake 30, and processes the detection signals sent from the sensors SR1 to SR3 to estimate whether the foot part 300 is in a walking cycle, that is, at any position in the stance phase and the swing phase.

The brake 30 brakes the rotation of the motor 10 by frictional force in accordance with a control signal sent from the controller 50. In the present embodiment, the controller 50 corresponds to, for example, a "control part", and the brake 30 corresponds to, for example, a "braking part".

Furthermore, the motor 10 operates, stops or changes the rotation speed according to the control signal sent from the controller 50, and thus adjusts the rotation speed of the deceleration mechanism transmitted from the motor.

(Specific Configuration)

Next, a more specific configuration of the assistance device 1 according to the present embodiment will be described with reference to FIG. 5A to FIG. 8B.

Figure 7B:
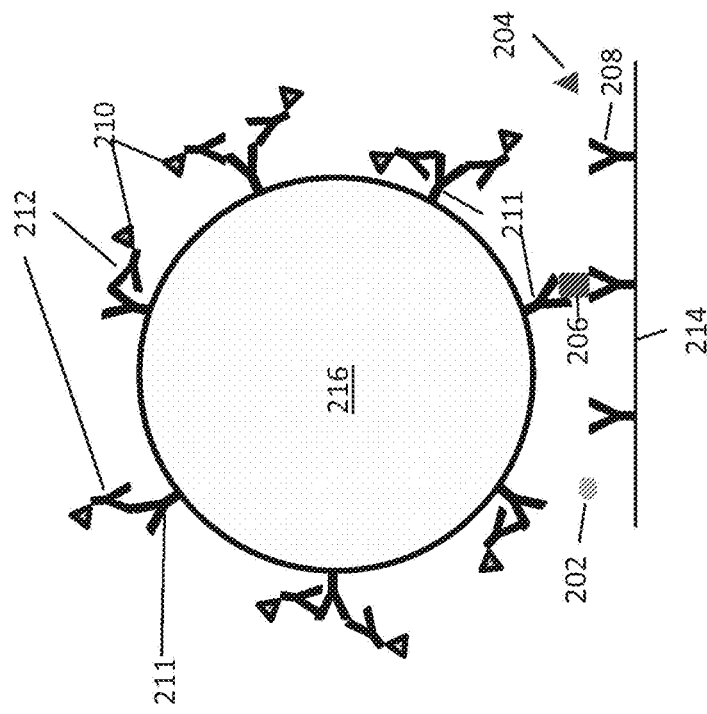
FIG. 7B is a cross-sectional view showing a state where the frame is removed from the configuration of FIG. 7A.
Figure 7A:
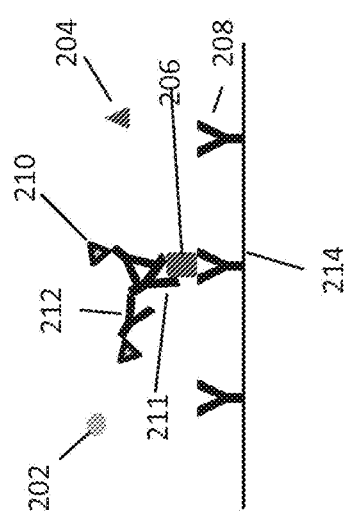
FIG. 7A is a cross-sectional view taken along the line B-B of FIG. 5A.
Figure 8A:
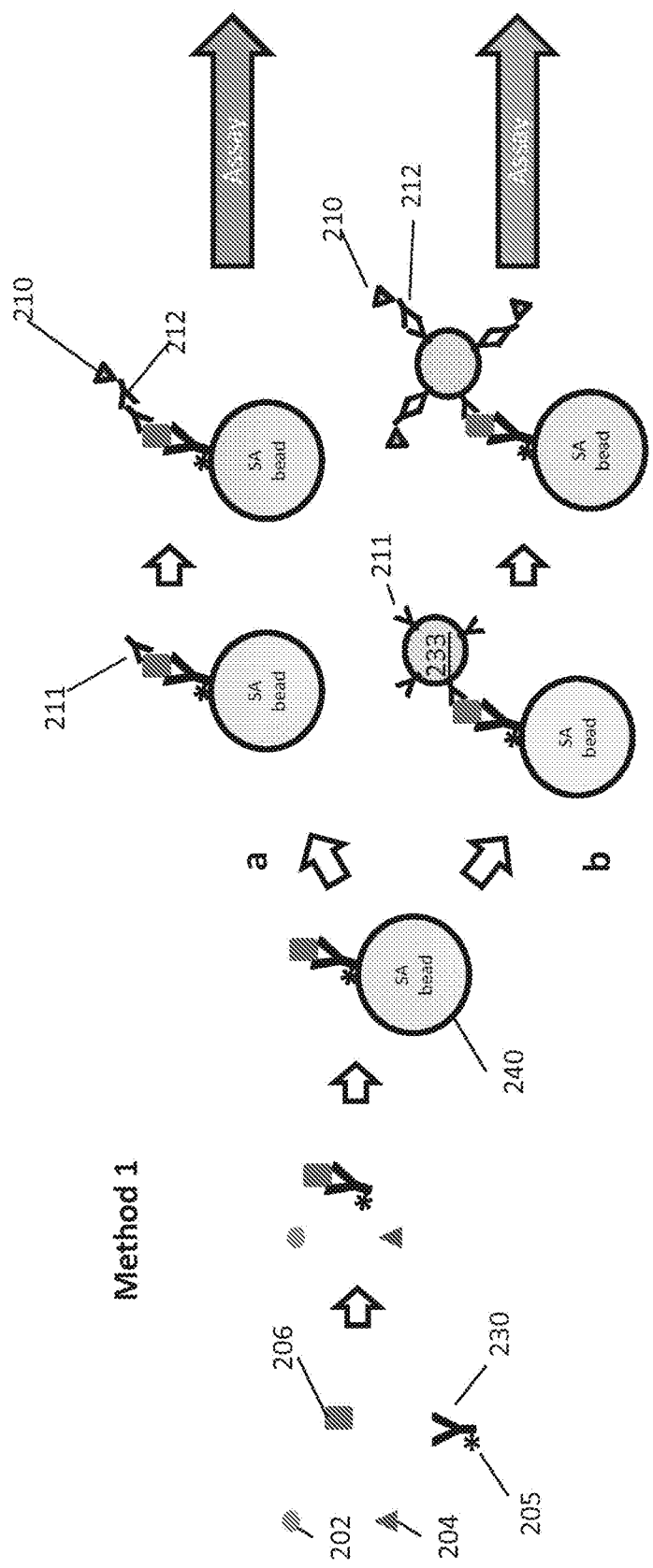
FIG. 8A is a left side view showing a specific configuration in a state where the frame is removed from the assistance device shown in FIG. 5A.
Figure 8D:
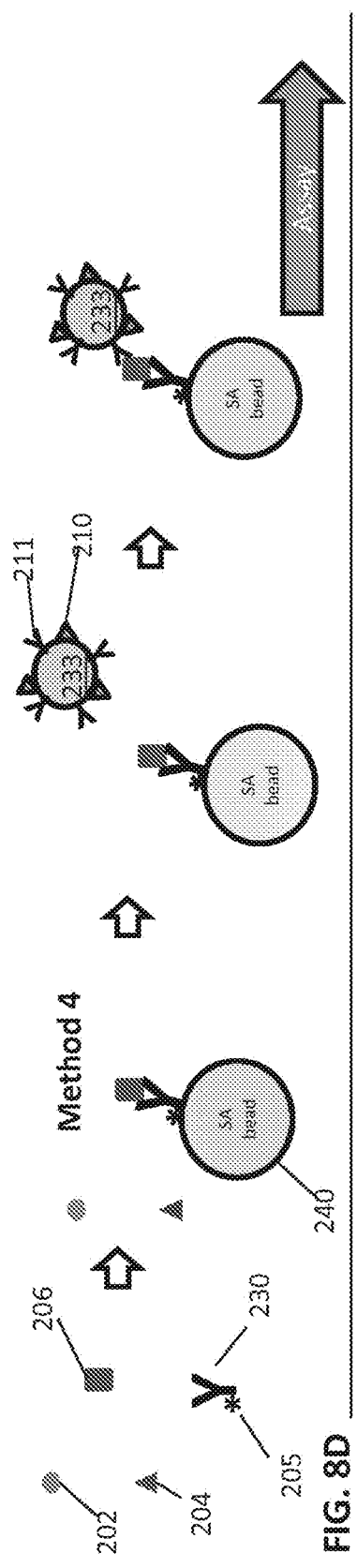
FIG. 8B is a left side view of the assistance device shown in FIG. 8A with some components are removed.
Figure 8E:
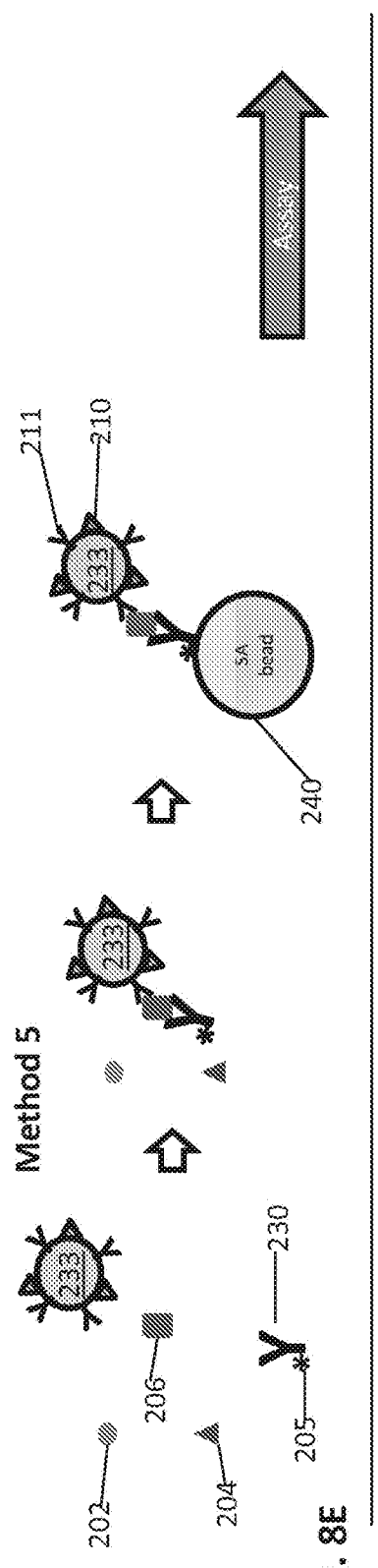
Figure 8F:
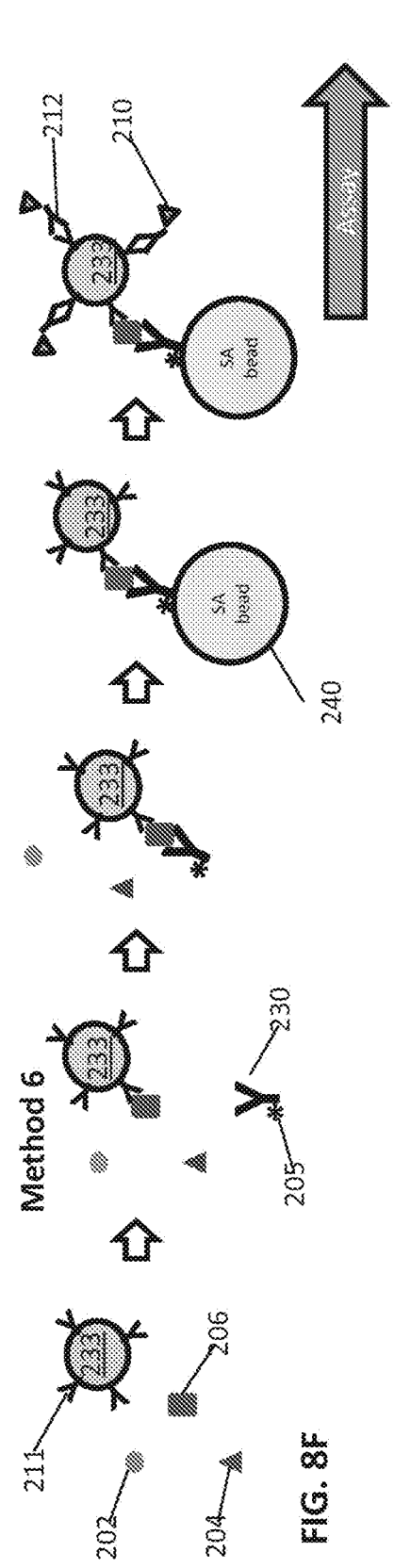

FIG. 5A is an example of a perspective view of the assistance device 1; FIG. 5B is an example of a perspective view showing a specific configuration in a state where the frame is removed from the assistance device shown in FIG. 5A; FIG. 6A is a cross-sectional view taken along the A-A line of FIG. 5A; FIG. 6B is an example of a front view showing a specific configuration in a state where the frame is removed from the assistance device shown in FIG. 5A; FIG. 7A is a cross-sectional view taken along the B-B line of FIG. 5A; and FIG. 7B is a cross-sectional view showing a configuration in a state where the frame is removed from the configuration of FIG. 7A. In addition, FIG. 8A is a left-side view showing a specific configuration in a state where the frame is removed from the assistance device shown in FIG. 5A, and FIG. 8B is a left-side view of a state where a part of the configuration is removed from the assistance device shown in FIG. 8A. It is to be noted that in FIG. 8A, an opening is virtually provided so that the control board can be visually recognized.

As shown in FIG. 5A to FIG. 8B, the assistance device 1 can be connected to a socket (not shown) by a pyramid connector provided on a top part thereof, and is configured to be connectable to the foot part 300 by the ankle part 24 provided on the bottom part thereof, thereby constituting an artificial foot. The frame 210 is arranged so as to cover from a part of the pyramid connector to a part of the ball screw support plate 270 (see FIG. 8A and FIG. 8B), thereby protecting the main part of the assistance device 1 from contact and collision with the outside.

The specific configuration of the assistance device 1 is as follows.

That is, the assistance device 1 includes a motor 10, a transmission mechanism 16, a ball screw 70, a slider crank 20, an ankle part 24, a brake 30, a controller 50, an IMU (Inertial Measurement Unit) sensor 501, an absolute encoder 502, and a force sensor SR3.

The IMU sensor 501 is a specific example of the inertia measuring sensor SR1. In the present embodiment, the IMU sensor 501 is built in on the control board CS in the controller 50, and detects the angular velocity and acceleration of the assistance device 1 to detect the advancing speed of the assistance device 1.

The absolute encoder 502 is a specific example of the angle sensor SR2 and is attached to the ankle part 24 to detect the ankle angle of the foot part 300.

The force sensor SR3 is attached to the upper part of the assistance device 1, and detects the magnitude of the repulsive force from the ground or the floor surface caused by the body weight that is applied to the foot part 300 by the wearer of the artificial foot. The force sensor SR3 also detects the rotation (twist) of the rear surface of the foot part 300 by detecting the Y-axis moment of the foot part 300.

The motor 10 is driven by power supply from a battery 60, and rotates the ball screw 70 in the forward and reverse direction via the transmission mechanism 16. It is to be noted that it is not necessary to incorporate a battery in the assistance device itself, and it is also possible to drive the motor 10 by power supply from the outside by using, for example, a commercial power source. As shown in FIG. 7, the ball screw 70 is fixed from above and below by a ball screw fixing plate 274 and a ball screw support plate 270. In the present embodiment, the motor 10, the transmission mechanism 16, and the ball screw 70 correspond to, for example, the "driving part".

In the present embodiment, as shown in FIG. 7, the brake 30 is attached to the upper end (socket side) of the rotation shaft of the motor 10, and receives a command signal from the controller 50 to be turned on, thereby delaying the operation of the motor 10 by a mechanical friction force. The brake 30 corresponds to, for example, the "braking part" in the present embodiment.

The ball nut 72 is configured to reciprocate in a linear direction in response to the rotation of the ball screw 70 in a vertical direction in FIG. 7.

The elastic part 18 is composed of two springs arranged vertically through a position corresponding to the ball nut 72, that is, is composed of a plantar flexion spring 181 and a dorsal flexion spring 182.

As shown in FIG. 8A and FIG. 8B, a linear guide LG includes a linear motion part 73 and a fixing part 74, and the elastic part 18 is configured to be connected to the linear motion part 73 via the fixing part 74 to move integrally.

The slider crank 20 converts the linear motion of the linear motion unit into a rotational motion to rotate the ankle part 24.

(Operation)

Next, the operation of the assistance device 1 according to the present embodiment will be described with reference to FIG. 9 to FIG. 13.

Figure 9:
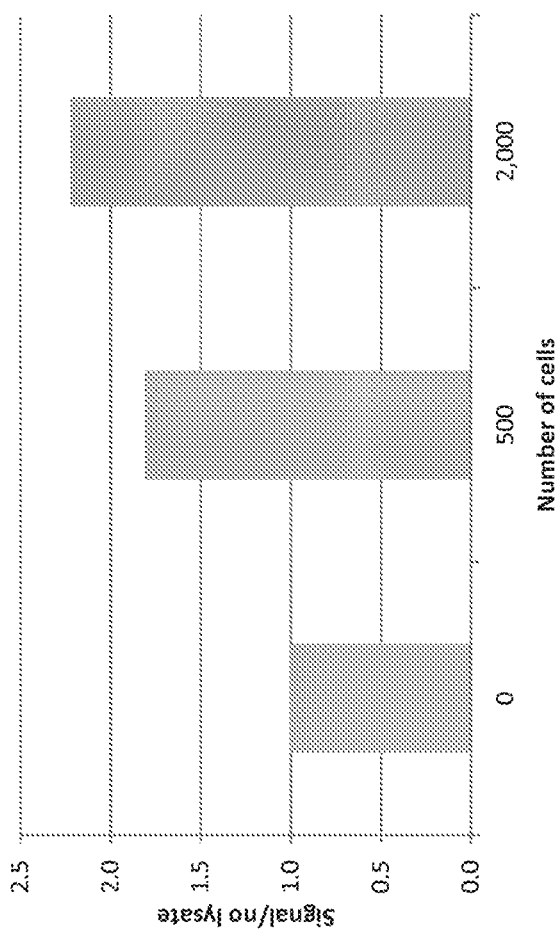
FIG. 9 is an explanatory diagram of the operation of the assistance device according to the first embodiment of the present invention.

FIG. 9 is an explanatory diagram of the operation of the assistance device according to the first embodiment of the present invention. The graph on the lower side of the drawing indicates the relationship between the ankle angle and the walking cycle, and the horizontal axis is composed of a stance phase A and a swing phase B and represents the elapsed time from the landing preparation of the foot part 300, and the vertical axis represents the ankle angle of the ankle part 24. As described with reference to FIG. 3, the ankle angle of 0° indicates a case where the direction of the rectilinear motion of the ball screw 70 by the driving part forms 90° with the ground or the floor surface, and this state is defined as a neutral state. In the present embodiment, the stance phase A corresponds to, for example, "the first phase", and the swing phase B corresponds to, for example, "the second phase".

The stance phase A is divided into a stance phase A1 to a stance phase A4 according to a walking stage. The stance phase A1 indicates a stage from the neutral state to a plantar flexion from the landing preparation until the landing. The stance phase A2 indicates a stage from the plantar flexion to substantially neutral state, in which the wearer starts moving the body weight from the rear end (heel part) toward the tip end (toe part) of the foot part 300 after landing, until the entire back surface of the foot part 300 comes into contact with the ground G. In addition, the stance phase A3 indicates a stage in which the ankle angle increases while shifting from the substantially neutral state to a dorsal flexion. The stance phase A4 indicates a stage in which the ankle angle becomes maximum and the foot part 300 kicks out (push off) the ground G, and then the ankle angle sharply decreases and the entire foot part 300 is finally separated from the ground G.

Figure 10D:
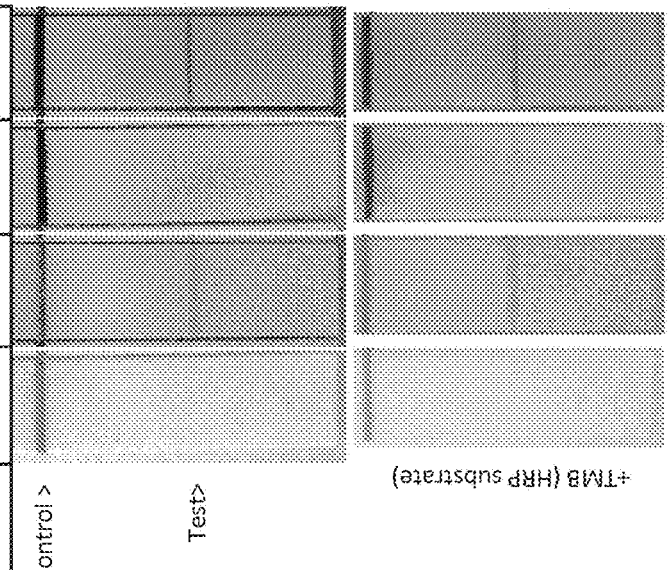
FIG. 10 is a block diagram for supplementing the description of FIG. 9.
Figure 10C:
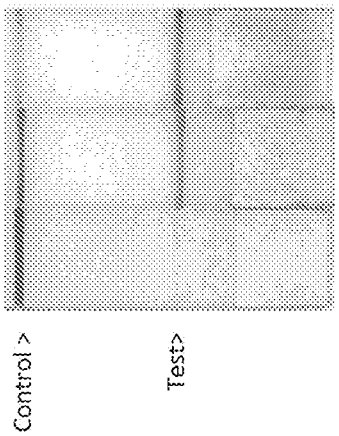

FIG. 10 is an example of a schematic diagram of a control flow of horizontal walking. P4 to P1 correspond to the stance phase A1, P1 to P2 correspond to the stance phase A2, P2 to P3 correspond to the stance phase A3, and P3 to P4 correspond to the stance phase A4.

The controller 50 estimates which walking stage the foot 300 is in by processing detection signals sent from the absolute encoder 502, the IMU sensor 501 and the force sensor SR3, and turns the brake 30 on and off.

First, it is estimated whether the foot part 300 is in the stance phase A or the swing phase B by processing the detection signal from the force sensor. This estimation corresponds to, for example, the "first stage" in this embodiment. In a case where it can be estimated that the foot part 300 is in the swing phase B (see P4 in FIG. 10), when the ankle angle becomes 0° by the detection signal from the absolute encoder 502, the controller 50 presumes that the wearer has started the landing preparation and sends a command signal to the brake 30 to turn on the brake 30.

Thus, the motor 10 is not operated due to the holding force of the brake 30. After the heel part of the foot part 300 is grounded, the ball nut 72 of the ball screw 70 does not move due to the holding force of the brake, and the plantar flexion spring 181 is compressed by the application of the body weight of the wearer, and the energy of gravity is accumulated in the spring. Thus, a plantar flexion angle of the stance phase A1 is realized (see P1 in FIG. 10). When entering the stance phase A2, the plantar flexion spring 181 is released and extended, and the ankle angle returns to the neutral state (0°). Also in the stance phase A3, the ball nut 72 does not move due to the holding force of the brake, but the dorsal flexion spring 182 compresses as the body weight moves forward, and the energy of gravity is accumulated in the spring 182. Thus, the dorsal flexion angle of the stance phase A3 is realized (see P2 in FIG. 10).

The controller 50 estimates which walking stage of the stance phase A3 the foot 300 is in by processing detection signals sent from the absolute encoder 502, the IMU sensor 501 and the force sensor SR3. More specifically, a value of Fz (vertical direction component of F) from the force sensor SR3, a value of My (moment in the Y-axis direction), and a value of the ankle angle from the absolute encoder 502 are compared with respective first reference values, and when all of the three values exceed the first reference values, the foot part 300 is estimated to be in the latter half of the stance phase A3. Subsequently, the controller 50 determines that the foot part 300 is moving forward by monitoring the value of the acceleration from the IMU sensor 501, and then monitors whether the wearer is applying a large amount of body weight from the value of Fz of the force sensor SR3 or the dorsal flexion angle becomes maximum from the value of the ankle angle of the absolute encoder 502, estimates that the foot part 300 has entered the stance phase A4 when each exceeds the second reference value, and sends a command signal to the brake 30 to turn off the brake 30. As a result, the motor 10 recovers the original rotational force, a large repulsive force is generated by the ankle part 24 via the transmission mechanism 16, the ball screw 70, and the slider crank 20, and the assistance device 1 moves forward by receiving a large energizing force in combination with the extension force caused by the release of the plantar flexion spring 181 (see P3 in FIG. 10).

Thus, the operation in which the relationship between the foot part 300 and the ground G is detected, and the on/off of the brake 30 is controlled corresponds to, for example, the "second stage" in this embodiment.

Thereafter, the foot part 300 enters the swing phase B (see P4 in FIG. 10) through the maximum plantar flexion angle, and after the neutral state, the brake is again turned on by a command signal from the controller 50. According to the present embodiment, a large power can be output at the time of kicking out even with a small motor, and energy efficiency is improved.

Mentioning the deceleration ratio of the assistance device 1 according to the present embodiment, the deceleration ratio by the slider crank 20 is expressed by the following expression.

$$K \frac{2\pi N b R}{2 L b N m}$$

Here, Nm is the number of teeth of the pulley on the side of motor 10 in the transmission mechanism 16, Nb is the number of teeth of the pulley on the side of the ball screw 70 in the transmission mechanism 16, Lb is the lead length of the ball screw 70, R is the arm length of the ankle part 24, and K is the deceleration coefficient by the slider crank 20.

The deceleration coefficient K of the slider crank is represented as follows.

$$K = \frac{\mathrm{Sin}(\alpha + \beta)}{\mathrm{Cos}\beta}$$

Figure 11:
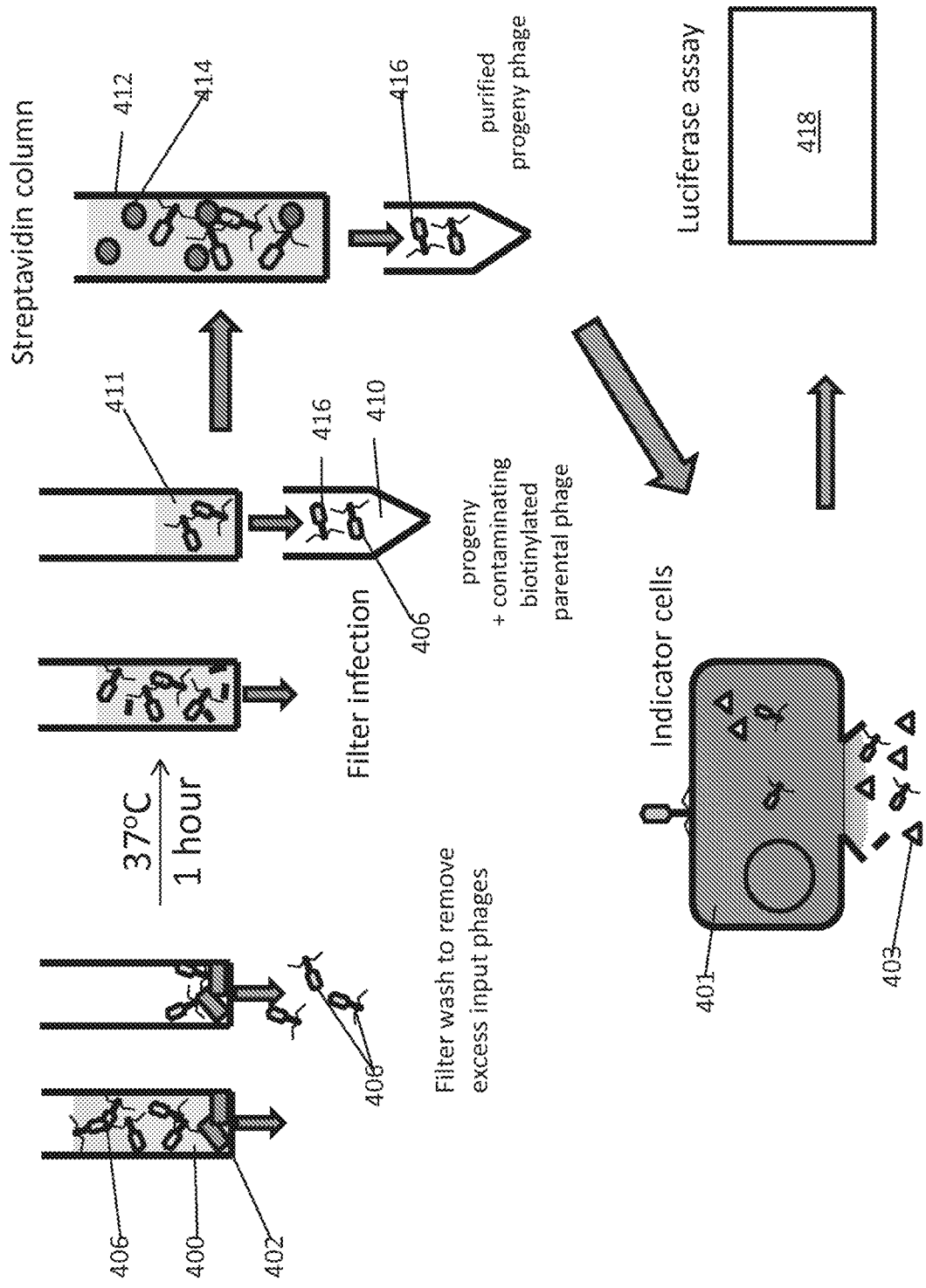
FIG. 11 is an explanatory diagram of a relationship between a crank mechanism for converting a linear motion into a rotational motion and its force according to the first embodiment of the present invention.
Figure 12A:
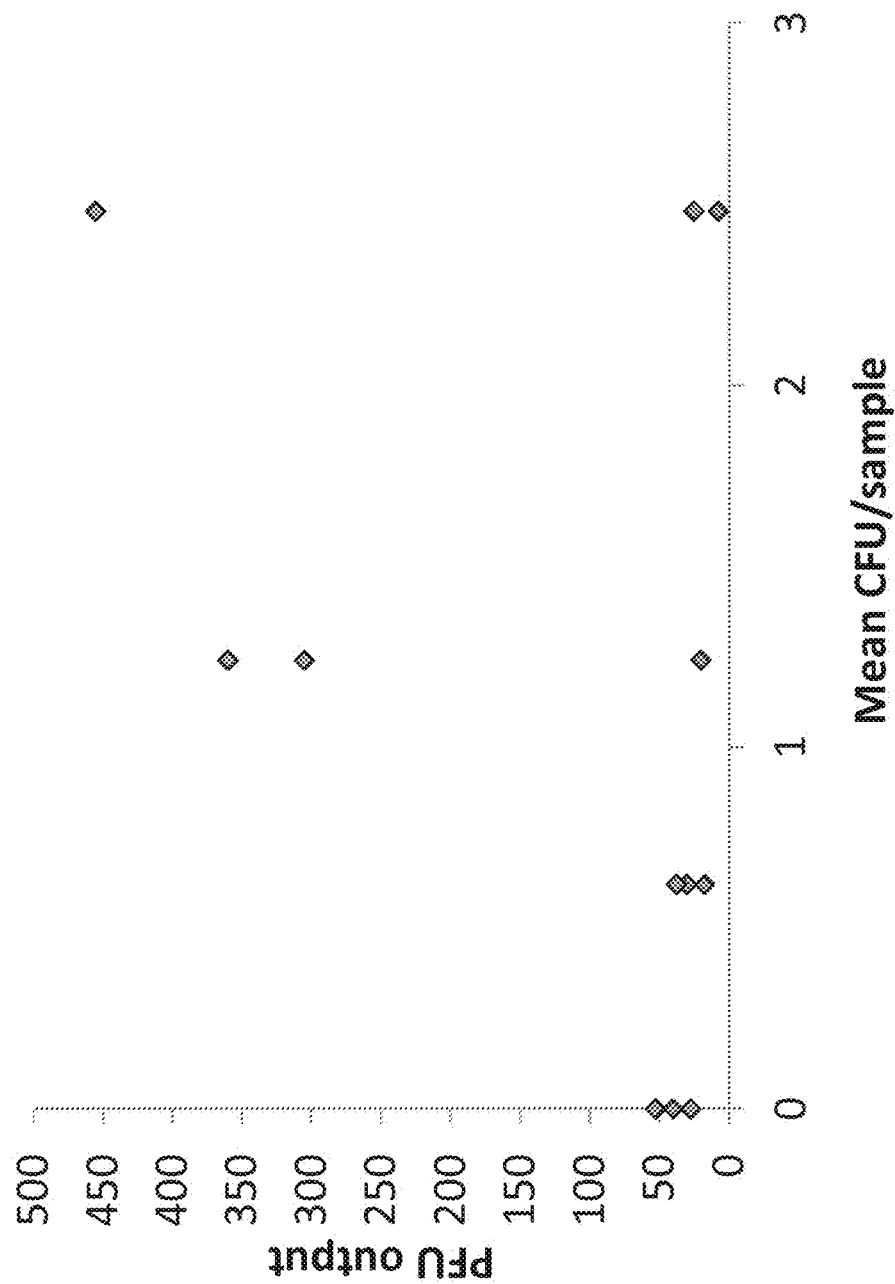
FIG. 12 is a diagram showing an example of a graph of a deceleration ratio in a slider crank under the influence of a deceleration coefficient.
Figure 12B:
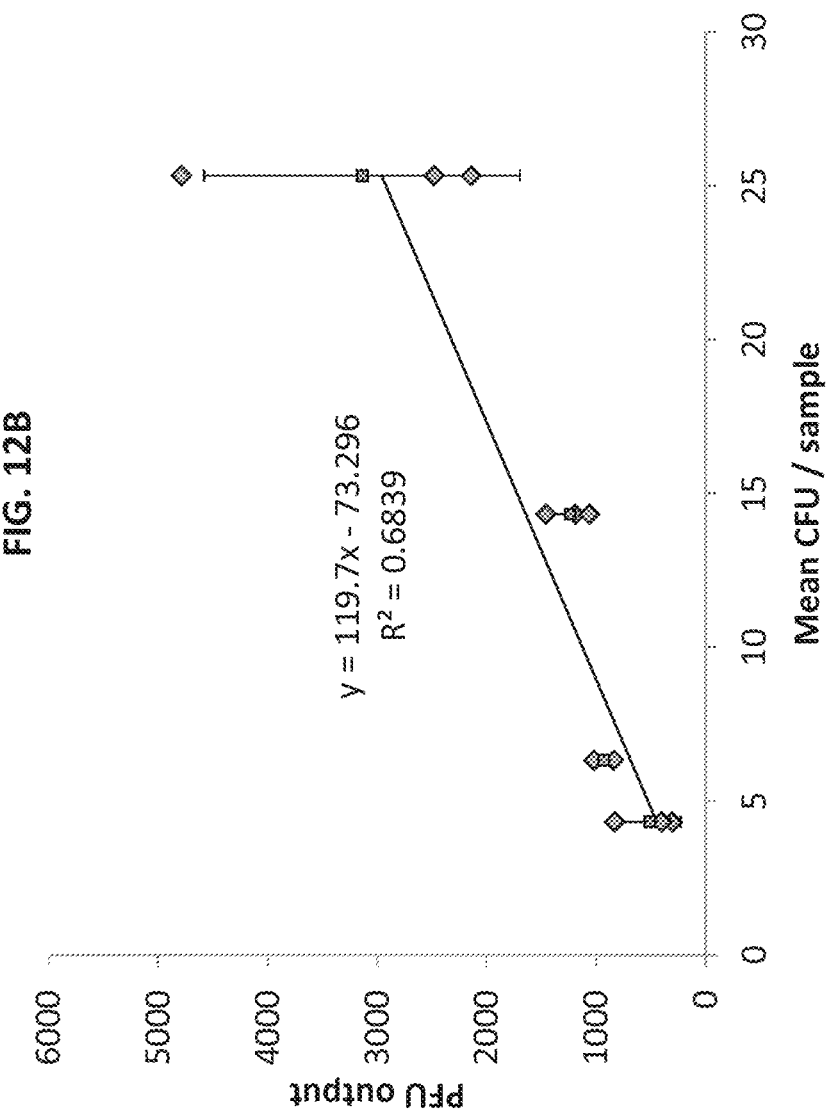
Figure 12D:
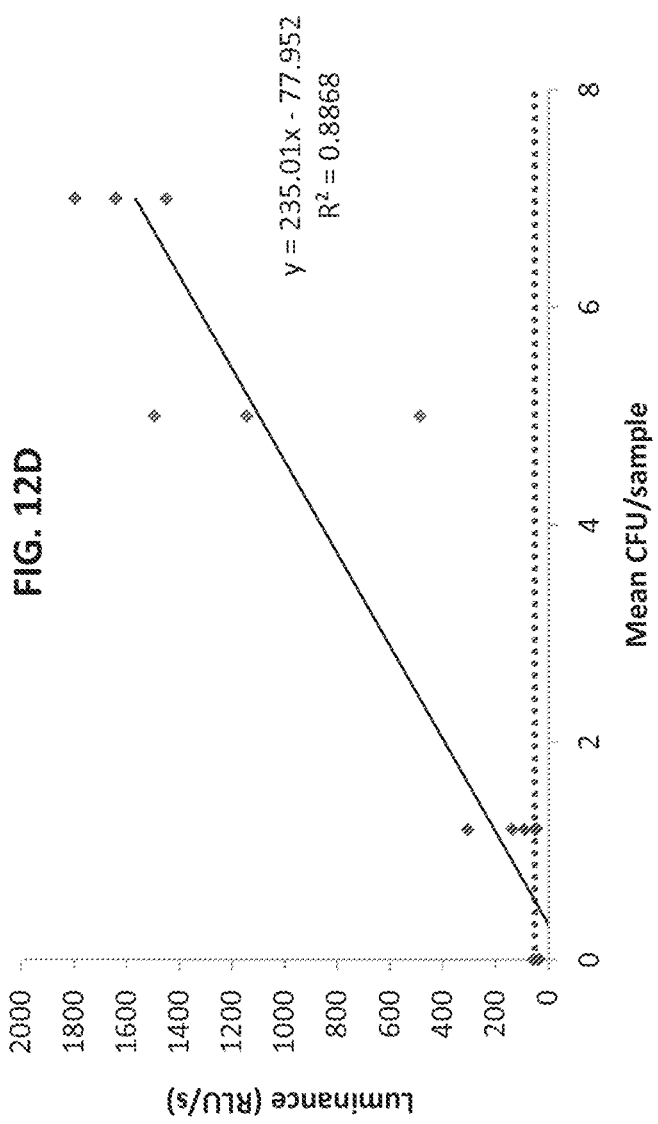

Here, as shown in FIG. 11, α is the angle between the arm of the ankle part 24 and the vertical direction, and β is the angle between the vertical direction and the rod 22. It is to be noted that, in FIG. 11, "$F_{SEA}$" is the force of the linear motion from the driving part, "L" is the length of the rod 22 of the slider crank 20, "R" is the length of the arm of the ankle part 24, and "D" is the offset from the center of the ankle part 24. The change in the deceleration ratio of the slider crank due to the influence of the deceleration coefficient K is shown in the graph of FIG. 12. Since there is a deceleration coefficient K of the slider crank, the deceleration ratio increases corresponding to the ankle angle, but when there is no K, the deceleration ratio is constant regardless of the ankle angle. By multiplying the motor torque by the deceleration ratio, the joint part torque by the motor can be calculated.

Figure 13:
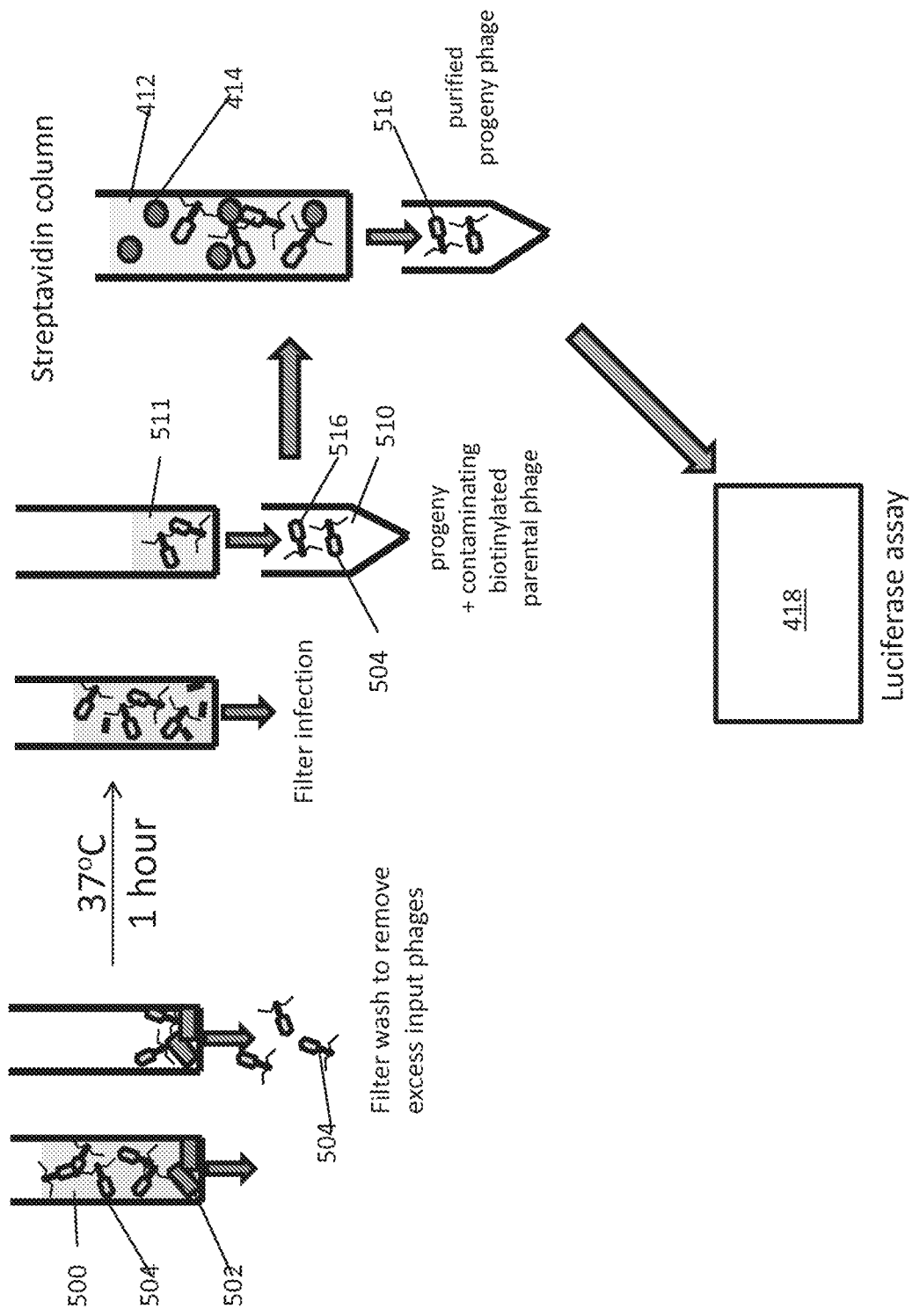
FIG. 13 is an example of a graph showing the relationship between the ankle angle and the torque applied to the ankle part by the motor.

FIG. 13 is an example of a graph showing the relationship between the ankle angle and the torque applied to the ankle part by the motor. In this figure, the horizontal axis represents the ankle angle of the ankle part 24, and the vertical axis represents the ankle part torque per 1 ampere of motor current. As shown in FIG. 13, the graph draws a gentle curve, and a value close to an ideal angular torque can be obtained. From this, it is understood that according to the assistance device 1 of the present embodiment, the torque up to the maximum dorsal flexion in FIG. 3 can also be output with a small current.

As described above, according to the assistance device of the present embodiment, the self-weight energy by the spring is accumulated, and when necessary, the energy is released together with the output of the motor, so that a large power can be output even with a small driving part, and the energy efficiency is improved. Also, the relationship between the angle of the joint part and the torque close to the human being can be mechanically realized, and the required torque can be reduced from the motor, so that the assistance device itself can be reduced in size and weight.

(Experimental Results)

Figure 14:
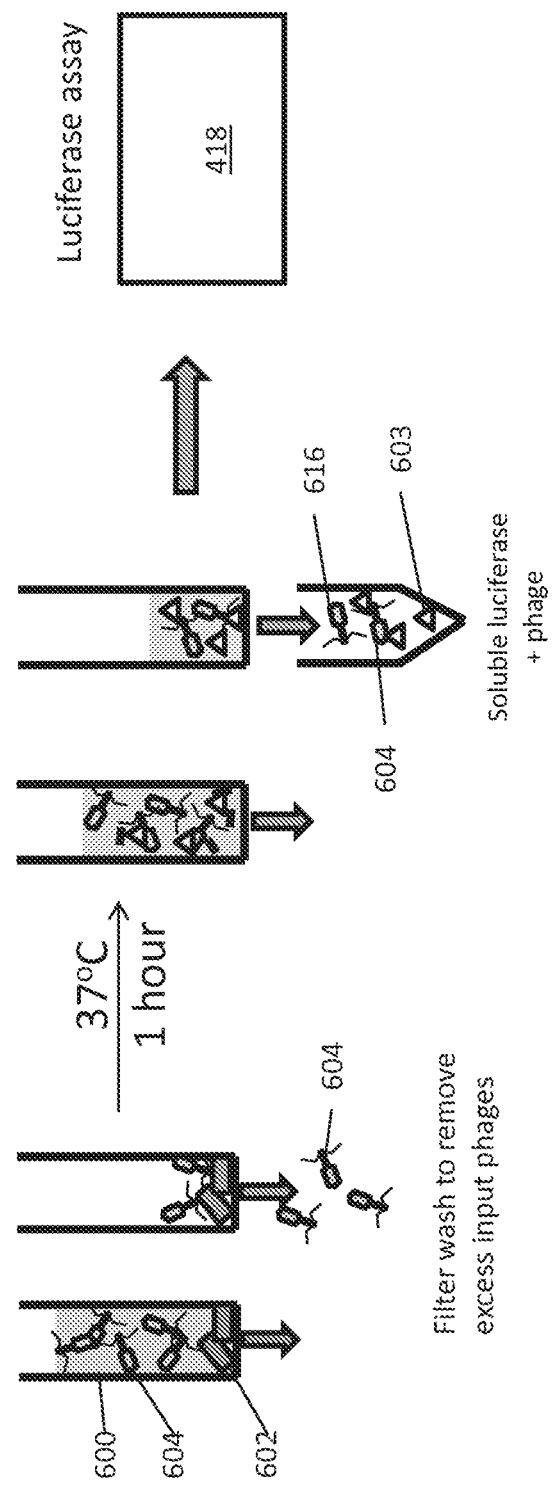
FIG. 14 is a photograph showing an appearance of a first subject who walks while wearing a trial product of the assistance device according to the first embodiment.
Figure 15:
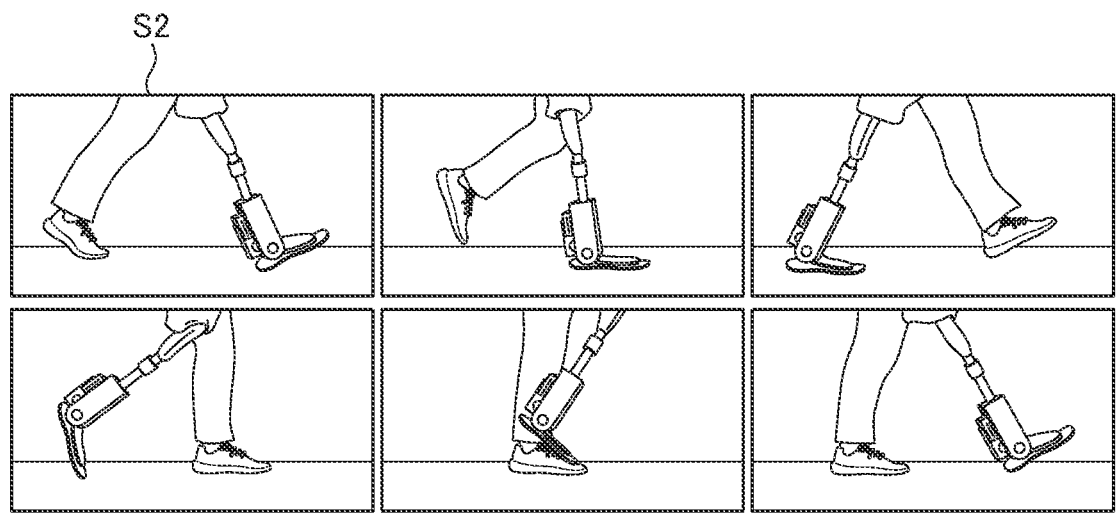
FIG. 15 is a photograph showing an appearance of a second subject who walks while wearing a trial product of the assistance device according to the first embodiment.
Figure 16:
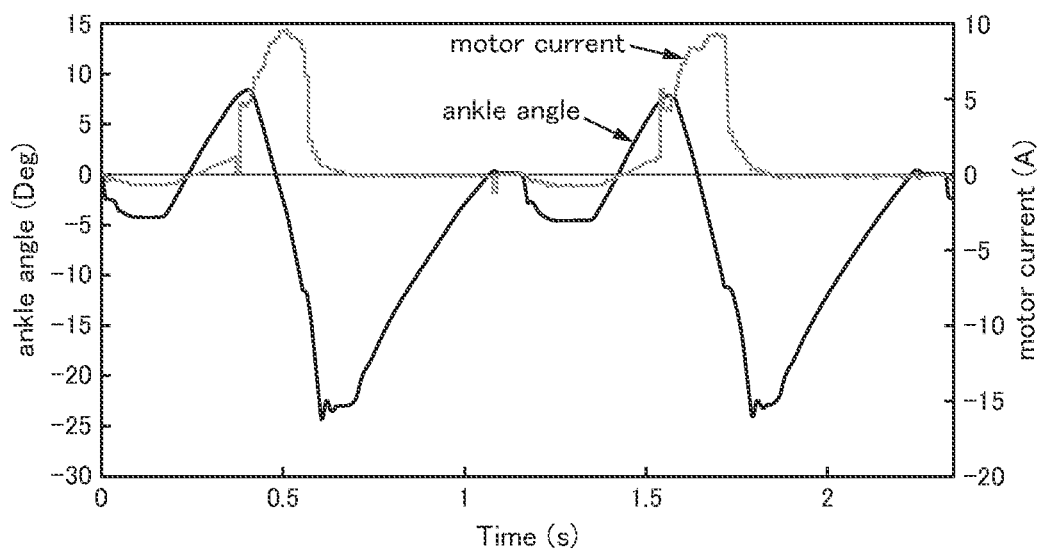
FIG. 16 is an example of a graph showing a result of performing plantar flexion at an ankle angle of around 4.5° and a motor current in an experiment of the subject of FIG. 14.
Figure 17:
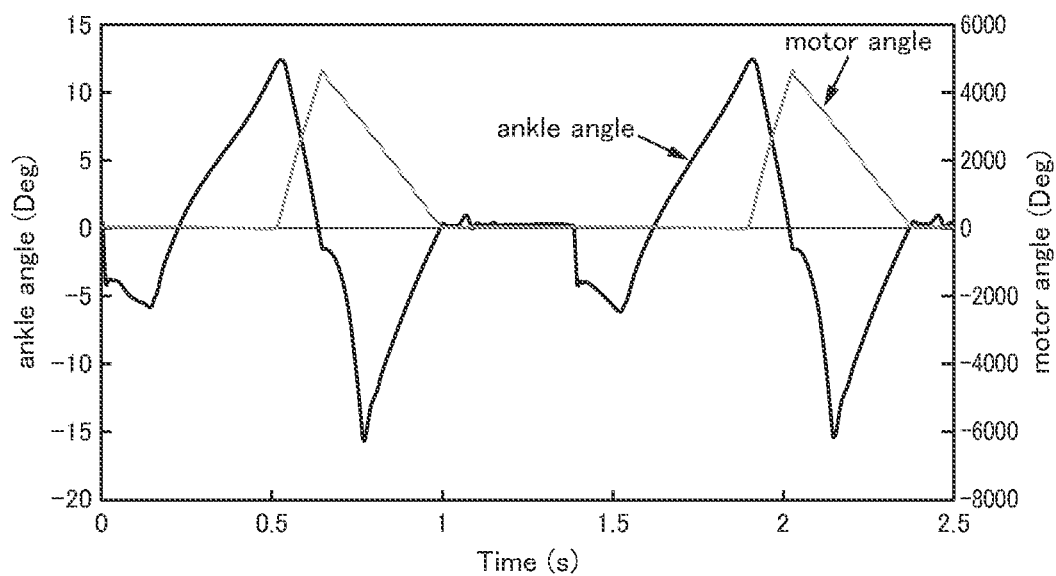
FIG. 17 is an example of a graph showing a result of performing plantar flexion at an ankle angle of around 5.5° and a motor current in the experiment of the subject of FIG. 15.

The experimental results obtained by using the trial products of the assistance device 1 according to the first embodiment are described below FIG. 14 and FIG. 15 are photographs showing a state in which two lower limb amputees S1 and S2 having different cutting sites wear the trial products of the assistance device 1 and walk on the treadmill. The lower limb amputees S1 and S2 are 25-year-old and 30-year-old men with a height of 180 cm and 170 cm and a body weight of 60 kg and 63 kg, walked on the treadmill at a speed per hour of 4.5 Km and 4 Km, respectively, and were measured with a sensor. FIG. 16 and FIG. 17 are examples of graphs showing the results of performing plantar flexion near the ankle angles of 4.5° and 5.5°, respectively, in order to increase the contact area between the foot and the ground after landing. In order to secure the neutral position of the motor, the angle of the motor is approximately 0°, and the plantar flexion near 4.5° and 5.5° is controlled by the flexion caused by the self-weight of the plantar flexion spring, and is helpful for absorbing the impact when the heel is grounded. After the initial plantar flexion, the spring is released and dorsal flexion begins until the ankle angle is neutral. The foot part is dorsiflexed with flexion due to the self-weight of the plantar flexion spring up to a maximum dorsal flexion of 8° and 12°. After the maximum dorsal flexion, the plantar flexion spring is released and returns to the neutral position. In this process the motor angle is still approximately 0°. When the foot part performs the second plantar flexion to the neutral position, the motor is used for push-off of the foot part, the ankle angle becomes the maximum plantar flexion, and the motor angle also becomes maximum. The ankle angle returns to the neutral position by the position control after the maximum plantar flexion.

Figure 18:
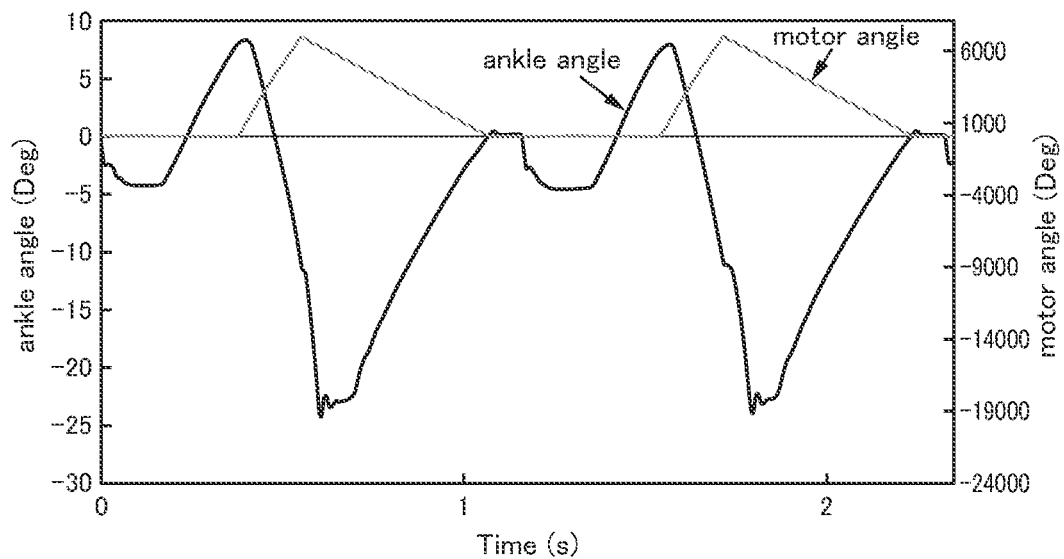
FIG. 18 is a diagram showing a change in a motor angle in a stance phase in an experiment of the subject of FIG. 14.
Figure 19:
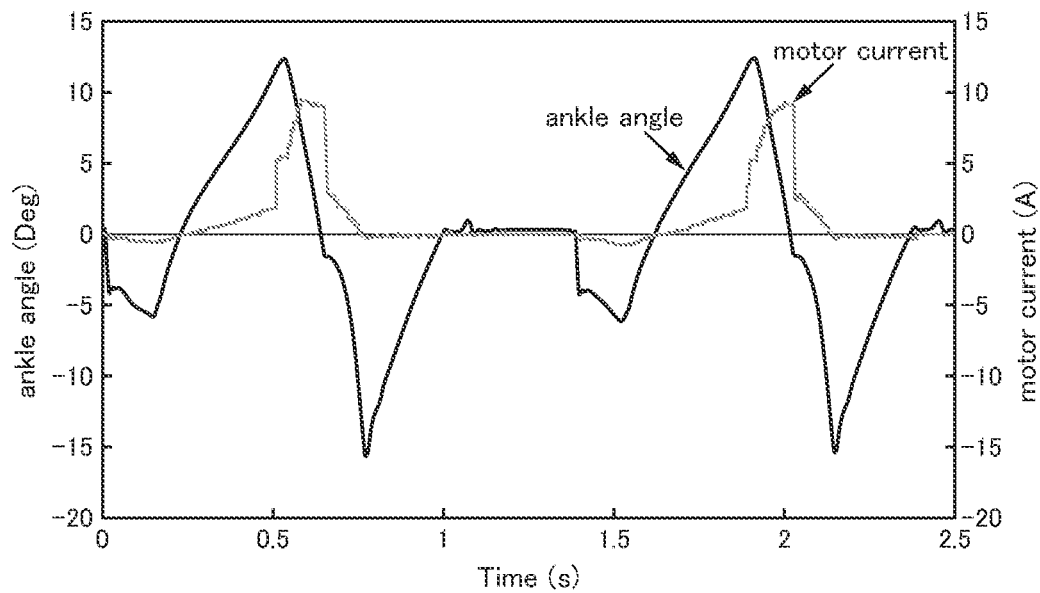
FIG. 19 is a diagram showing a change in a motor angle in a stance phase in an experiment of the subject of FIG. 15.

FIG. 18 and FIG. 19 show that the motor current is very small from the stance phase A1 to the stance phase A3 and the motor current becomes a peak at the maximum plantar flexion in the stance phase A4.

Figure 20:
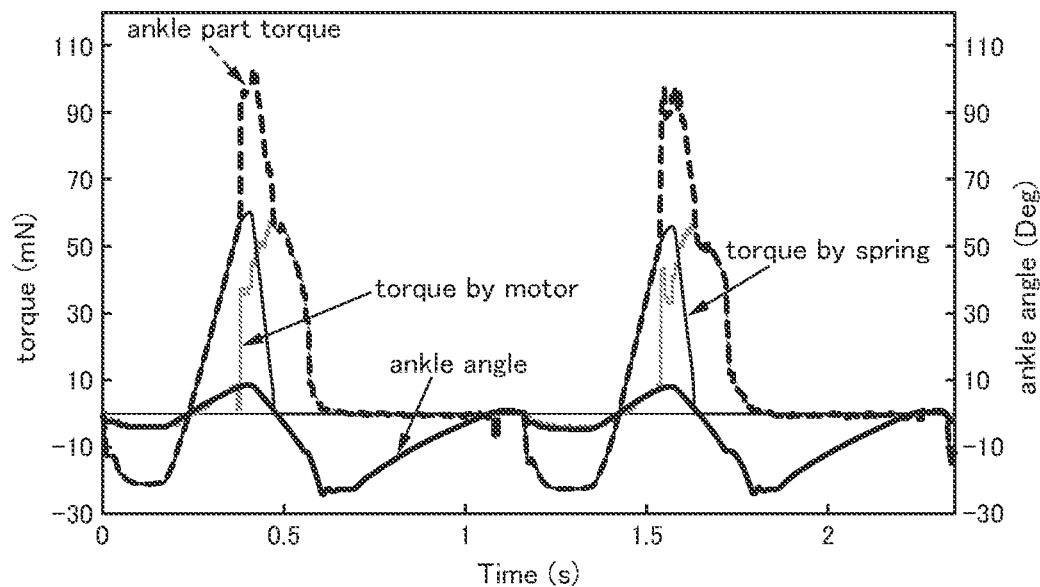
FIG. 20 is an example of a graph showing an ankle part torque contributed by a motor and a spring in the experiment of the subject of FIG. 14.
Figure 21:
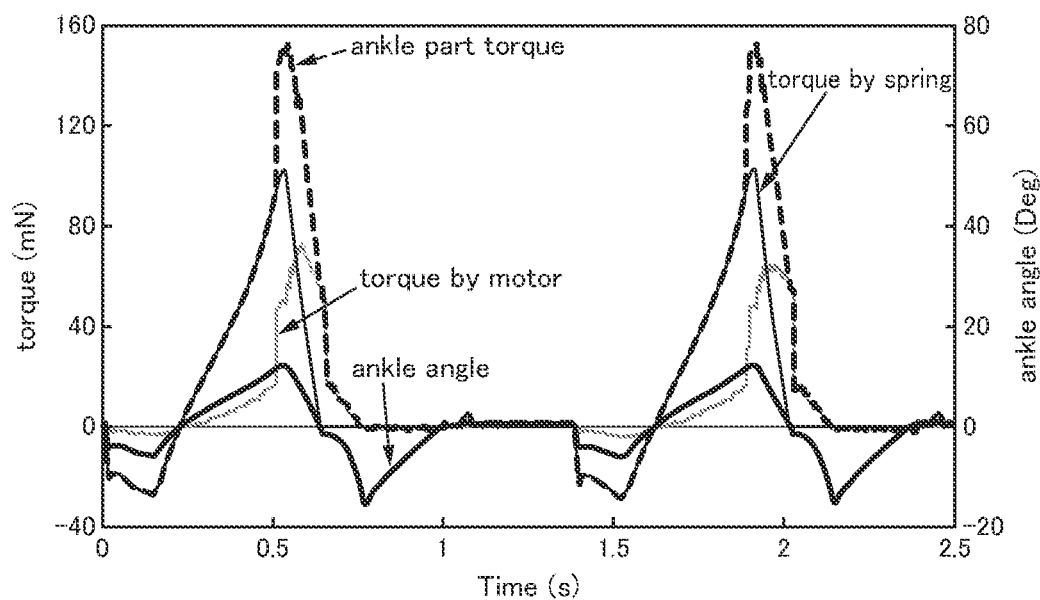
FIG. 21 is an example of a graph showing an ankle part torque contributed by a motor and a spring in the experiment of the subject of FIG. 15.
Figure 22:
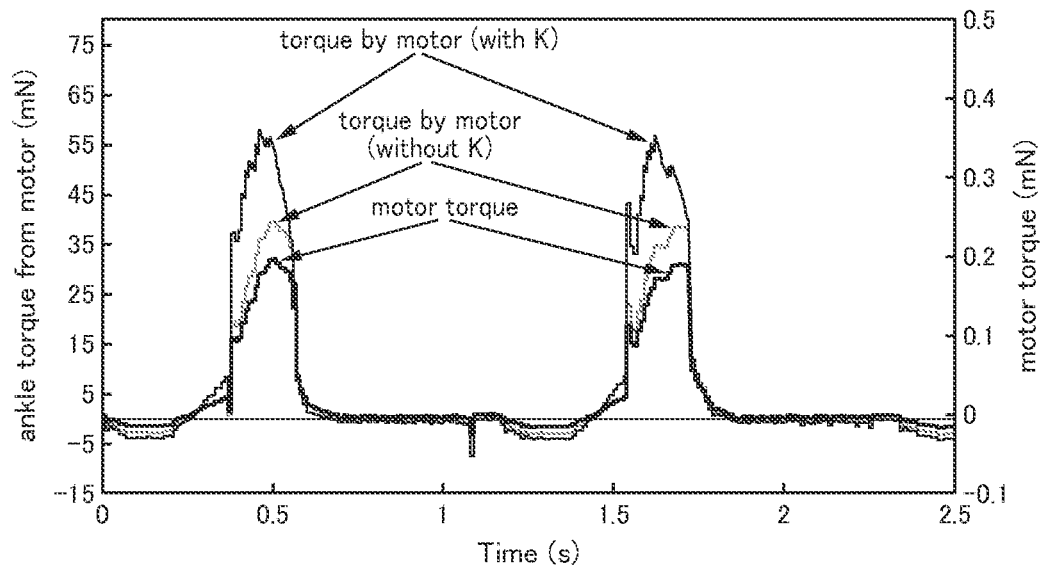
FIG. 22 is an example of a graph showing the ankle part torque contributed by the motor in the difference between the case where the transmission coefficient K is present and the case where the transmission coefficient K is not present in the first experiment of the subject of FIG. 14.
Figure 23:
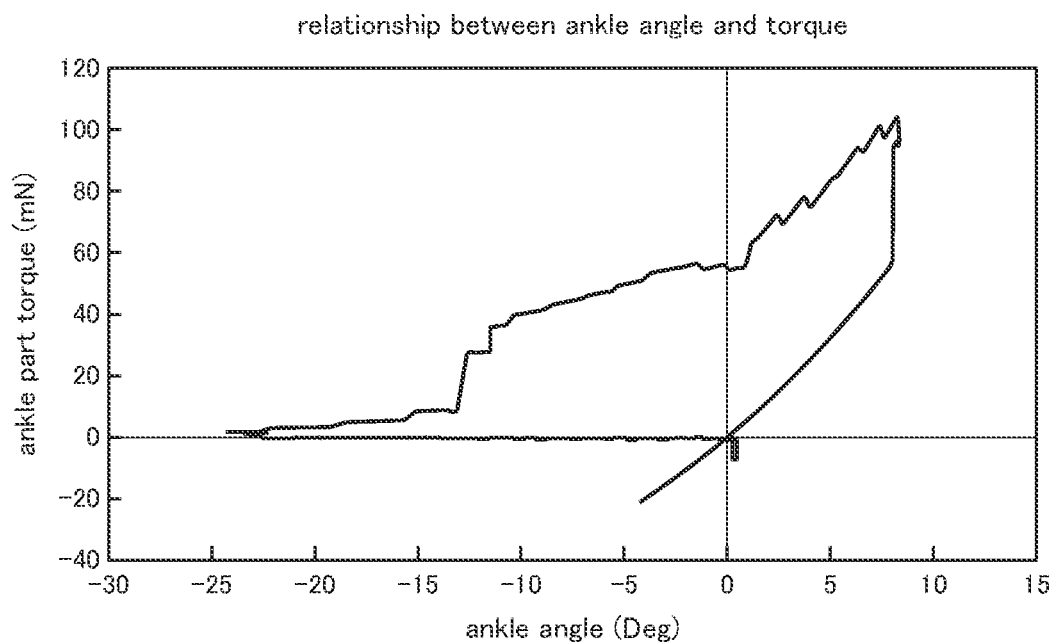
FIG. 23 shows a relationship between a torque and an angle in one walking cycle in the experiment of the subject of FIG. 14.
Figure 24:
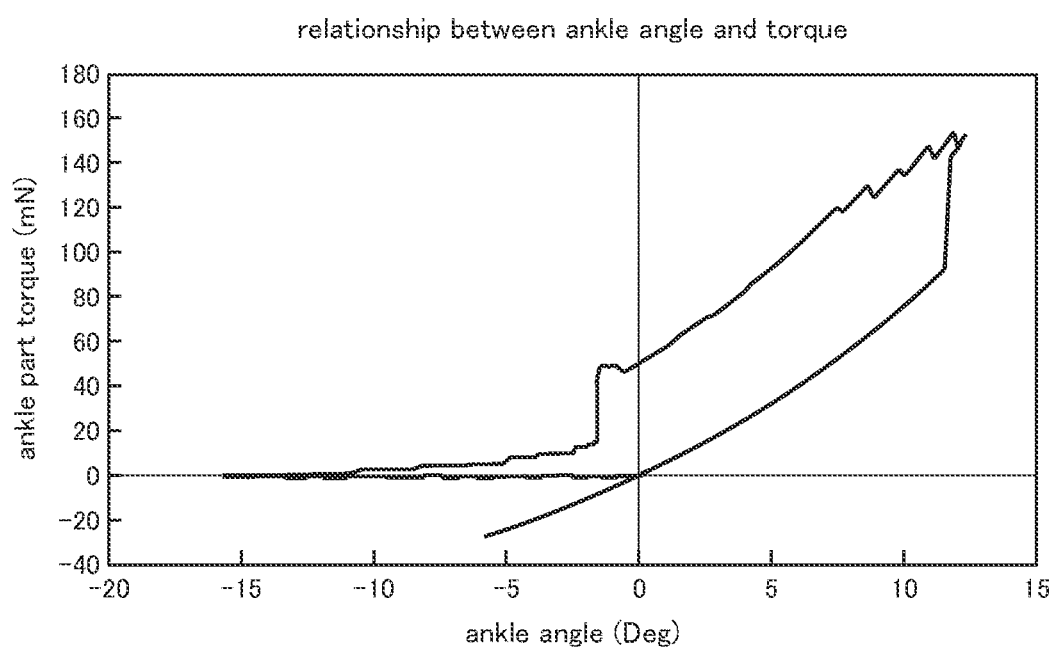
FIG. 24 shows a relationship between a torque and an angle in one walking cycle in the experiment of the subject of FIG. 15.

FIG. 20 and FIG. 21 are examples showing the ankle torque contributed by the motor and the spring and the total ankle torque for each of the subjects S1 and S2. Although the body weights of the subjects S1 and S2 are not significantly different, the maximum torque of the ankle part is entirely different because the torque of the spring is different. Since the maximum dorsal flexion in each experiment is about 8° and about 12°, the torque of the spring is entirely different. The ankle part torque given by the motor is different due to the deceleration coefficient K shown in FIG. 22. Larger torque is obtained in the energized plantar flexion, indicating that variable deceleration ratio by this mechanism is superior, because it reduces the required motor torque, compared to conventional mechanisms. FIG. 23 and FIG. 24 show the relationship between the torque and the angle in one walking cycle in the experiments of the subjects S1 and S2, respectively. It is to be noted that in the stance phase A3, the plantar flexion spring is compressed by the body weight of the subject, energy is accumulated in the spring and is released after the maximum dorsal flexion, and the torque of the ankle part is given by the plantar flexion spring at the maximum dorsal flexion. This indicates that the energy released by the dorsal flexion spring may weaken the power required from the motor in the energized dorsal flexion and store the system energy in this phase. A clinical feedback that the push-off from the repulsive force of the trial product can help the subject move forward more easily is obtained.

Modification Example

Figure 25:
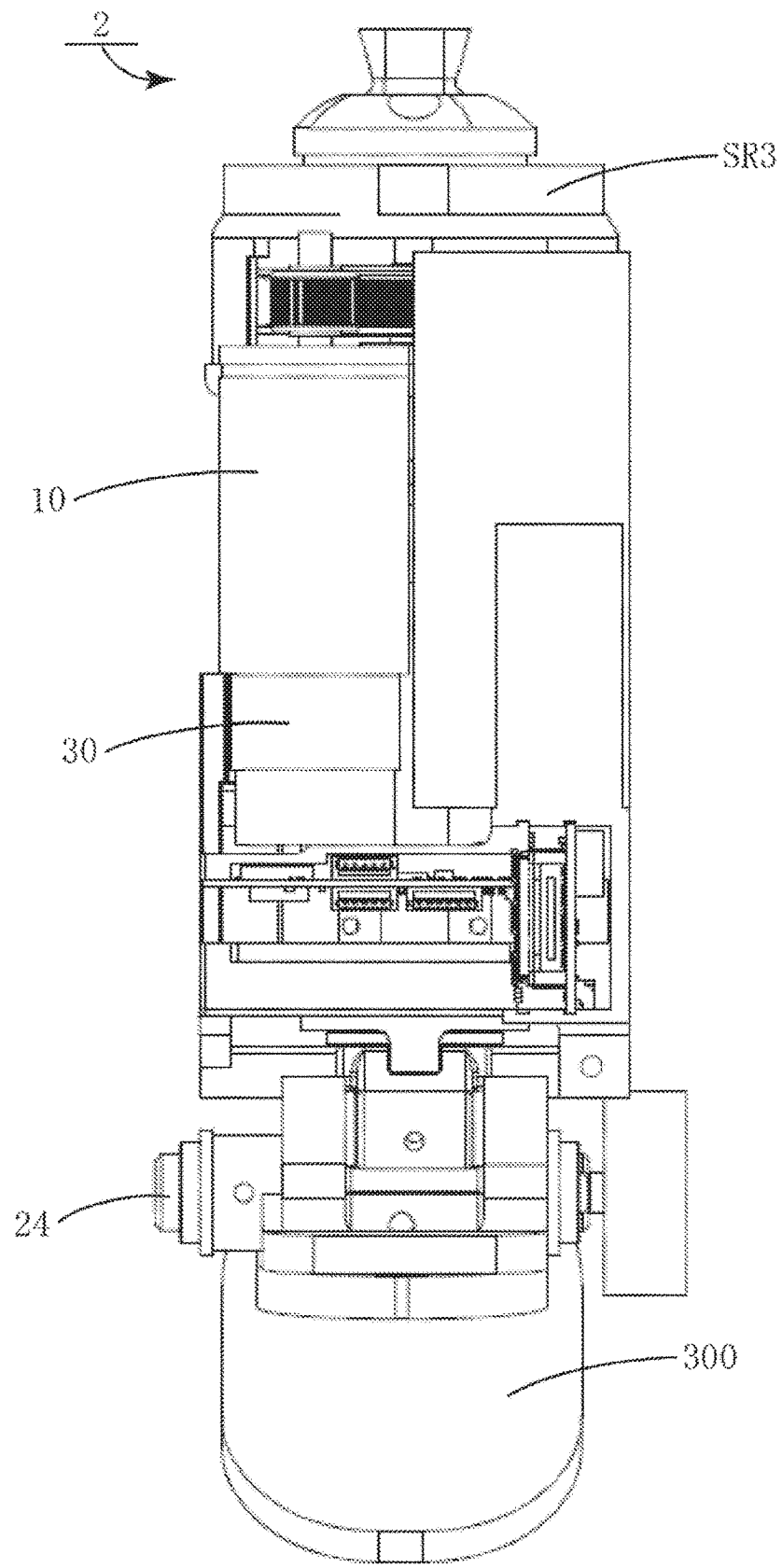
FIG. 25 is an example of a block diagram showing a main configuration of an assistance device according to a Modification Example of the first embodiment.

In the above-described embodiment, an example in which the brake 30 is attached to the upper end (socket side) of both ends of the rotation shaft of the motor 10 has been described, but the position of the brake 30 is not limited to this, and for example, like the assistance device 2 shown in FIG. 25, it may also be attached to the lower end (foot part) of the rotation shaft of the motor 10. The other configurations of the assistance device 2 are substantially the same as those of the assistance device 1 described above, and the control method, operation, and effect thereof are also substantially the same, and therefore the repetitive description will be omitted.

(2) Second Embodiment

In the above-described embodiment, the rotation speed of the motor 10 is reduced by the mechanical frictional force by using the brake 30 as the braking part of the motor 10, but the braking means of the motor 10 is not limited to this, and for example, there is also a method in which the rotation energy of the motor is converted into electric energy by a short circuit of the motor 10, and thereby the rotation of the motor is braked. Hereinafter, an embodiment of the assistance device having such a configuration will be taken up and described.

Figure 26:
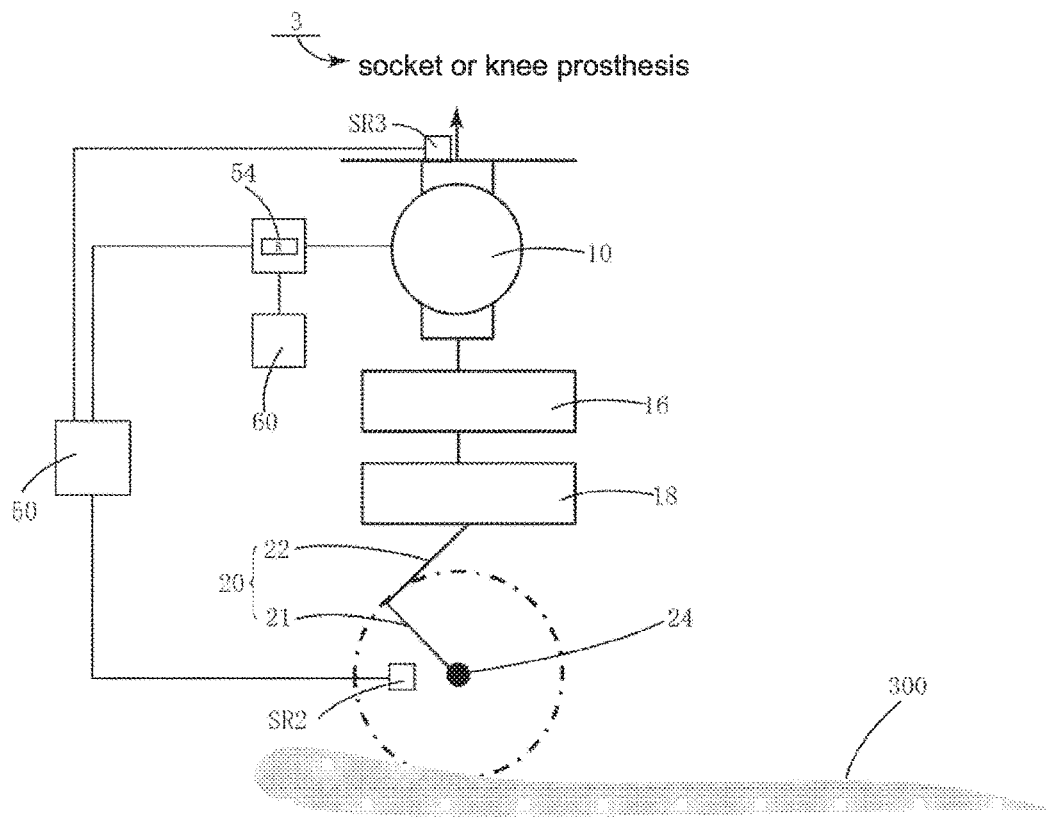
FIG. 26 is an example of a front view showing a main configuration of an assistance device according to the second embodiment of the present invention.

FIG. 26 is an example of a block diagram showing a main configuration of an assistance device 3 according to the second embodiment of the present invention. As is clear from comparison with FIG. 4, the assistance device 3 of the present embodiment includes a route switching part 54 in place of the brake 30 in the configuration of the assistance device 1 according to the first embodiment. The route switching part 54 includes a resistor R, is provided between the motor 10 and the battery 60, is connected to the controller 50, and is supplied with a control signal from the controller 50 to switch connection/non-connection between the motor 10 and the battery 60.

Figure 27:
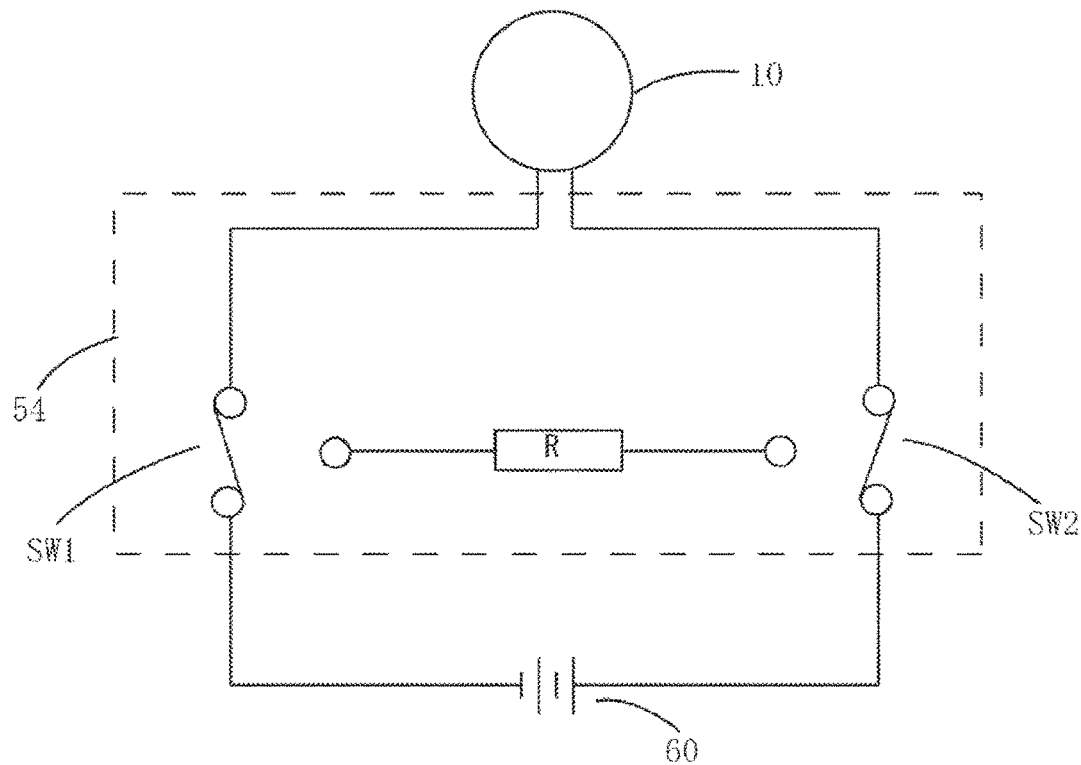
FIG. 27 is a circuit diagram showing a more specific configuration of a route switching part included in the assistance device shown in FIG. 26.
Figure 28:
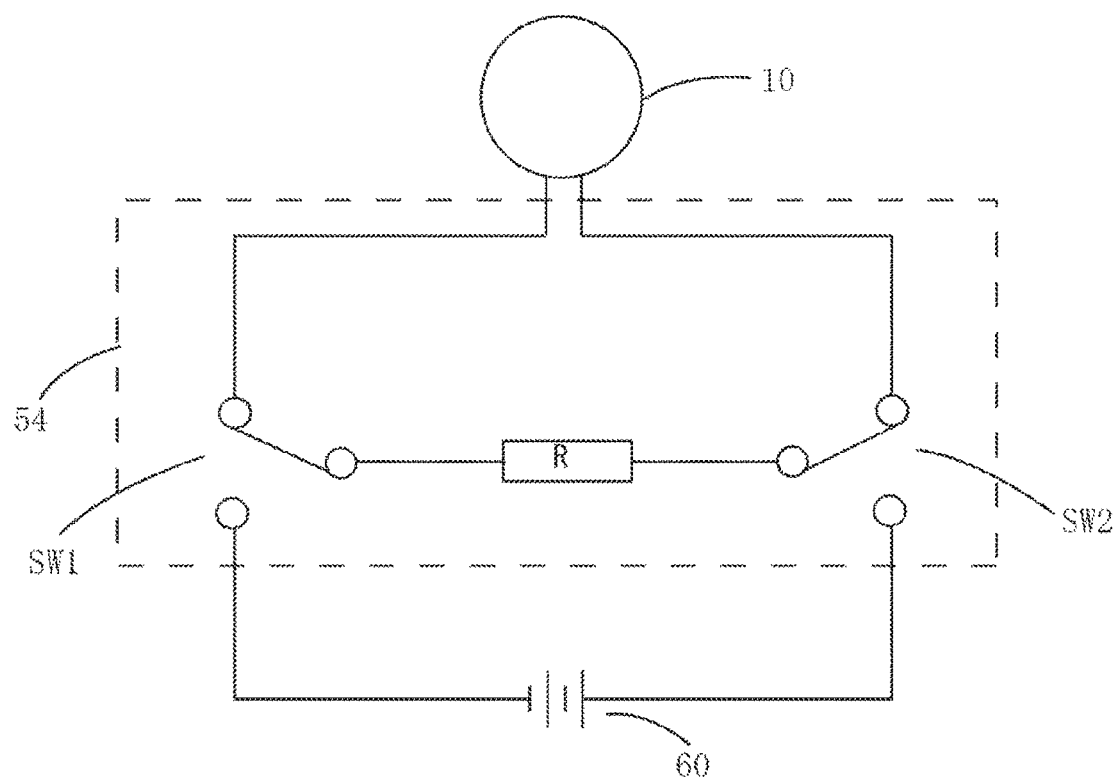
FIG. 28 is a circuit diagram showing a more specific configuration of a route switching part included in the assistance device shown in FIG. 26.

FIG. 27 and FIG. 28 are circuit diagrams showing a more specific configuration of the route switching part 54. The route switching part 54 includes change-over switches SW1 and SW2 and a resistor R. When the braking of the motor 10 is not performed (corresponding to the brake-off in the first embodiment), as shown in FIG. 27, the change-over switches SW1 and SW2 connect the motor 10 and the battery 60, and the connection between both terminals of the resistor R and the motor 10 is opened to realize power supply from the battery 60 to the motor 10. On the other hand, when the braking of the motor 10 is performed (corresponding to the brake-on in the first embodiment), as shown in FIG. 28, the connection between the battery 60 and the motor 10 is opened to connect both terminals of the resistor R and the motor 10. Thus, the motor 10 is brought in to a short-circuit state, the motor 10 becomes a power generator, and the rotational energy at the time of switching is converted into electric energy, so that the motor 10 is braked. The value of the resistor R can be arbitrarily determined according to the degree of braking required. The route switching part 54 corresponds to, for example, the "switching part" in the present embodiment. Since the other configurations, operations, and control modes of the assistance device 3 of the present embodiment are substantially the same as those of the assistance device 1 shown in FIG. 4, redundant description is omitted.

According to the control method of the assistance device according to the above-described embodiment, it becomes possible to output a large power even with a small driving part, and the energy efficiency is improved. In addition, the relationship between the angle of the joint part and the torque, which is close to that of a human, can be realized, and safe operation can be realized.

(3) Third Embodiment

Figure 29:
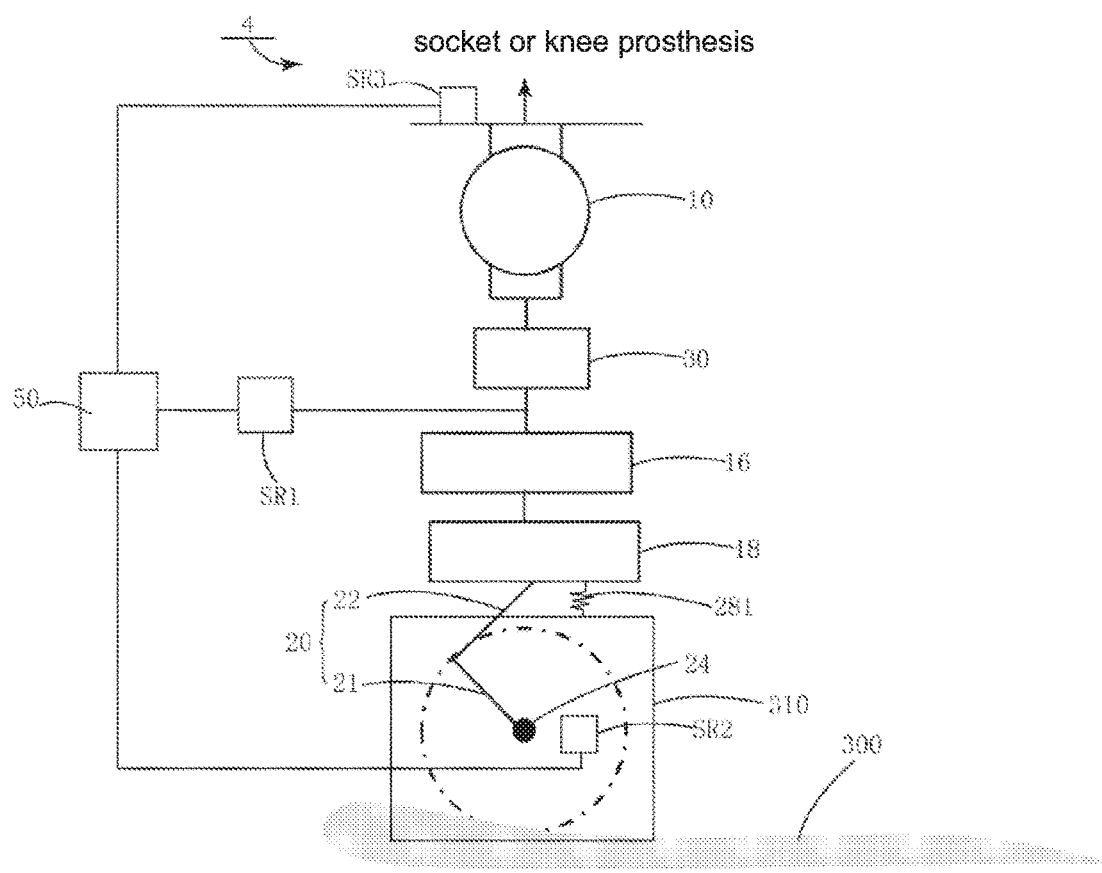
FIG. 29 is an example of a block diagram showing a main configuration of an assistance device according to the third embodiment of the present invention.

An example of a block diagram showing a main configuration of an assistance device according to the third embodiment of the present invention is shown in FIG. 29.

In the above-described embodiment, as the elastic part, the plantar flexion spring 181 and the dorsal flexion spring 182 are arranged to be connected in series between the transmission mechanism and the crank mechanism, for example, in the cylinder 90 (see FIG. 7A), and self-weight energy is accumulated by these springs. When necessary, the energy is released together with the output of the motor to assist the kicking out.

However, it is preferable that there is more energizing force by such springs. The assistance device 4 shown in the present embodiment further includes a parallel spring provided in parallel with the driving part or the crank mechanism between the driving part and the foot part, for example, between the driving part and the ankle part, in addition to the plantar flexion spring 181 and the dorsal flexion spring 182 in the cylinder 90.

More specifically, a joint frame 310 is provided on the foot part 300 so as to cover the ankle part 24, and a parallel spring 281 is mounted between the top surface of this joint frame 310 and the bottom surface of the cylinder 90 accommodating the ball screw 70 of the driving part. The other configurations of the assistance device 4 of the present embodiment are substantially the same as those of the assistance device 1 shown in FIG. 4.

The material of the parallel spring 281 may be the same as the plantar flexion spring 181 and the dorsal flexion spring 182 in the cylinder 90, or may be a material having more excellent compressive/repulsive force.

According to the present embodiment, by arranging such a parallel spring between the foot part 300 and the cylinder 90, further energizing force can be obtained during walking operation, and smoother and safer walking becomes possible. In addition, since the load of the motor is also reduced correspondingly by the additional energizing force by the parallel spring, it is possible to realize further energy efficiency and device weight reduction.

Modification Example

In the present embodiment shown in FIG. 29, an example is taken up in which the parallel spring 281 is mounted between the bottom surface of the cylinder 90 and the top surface of the joint frame 310, but the arrangement position of the parallel spring is not limited to this, and may be arranged, for example, between the joint frame and the foot part.

Figure 30:
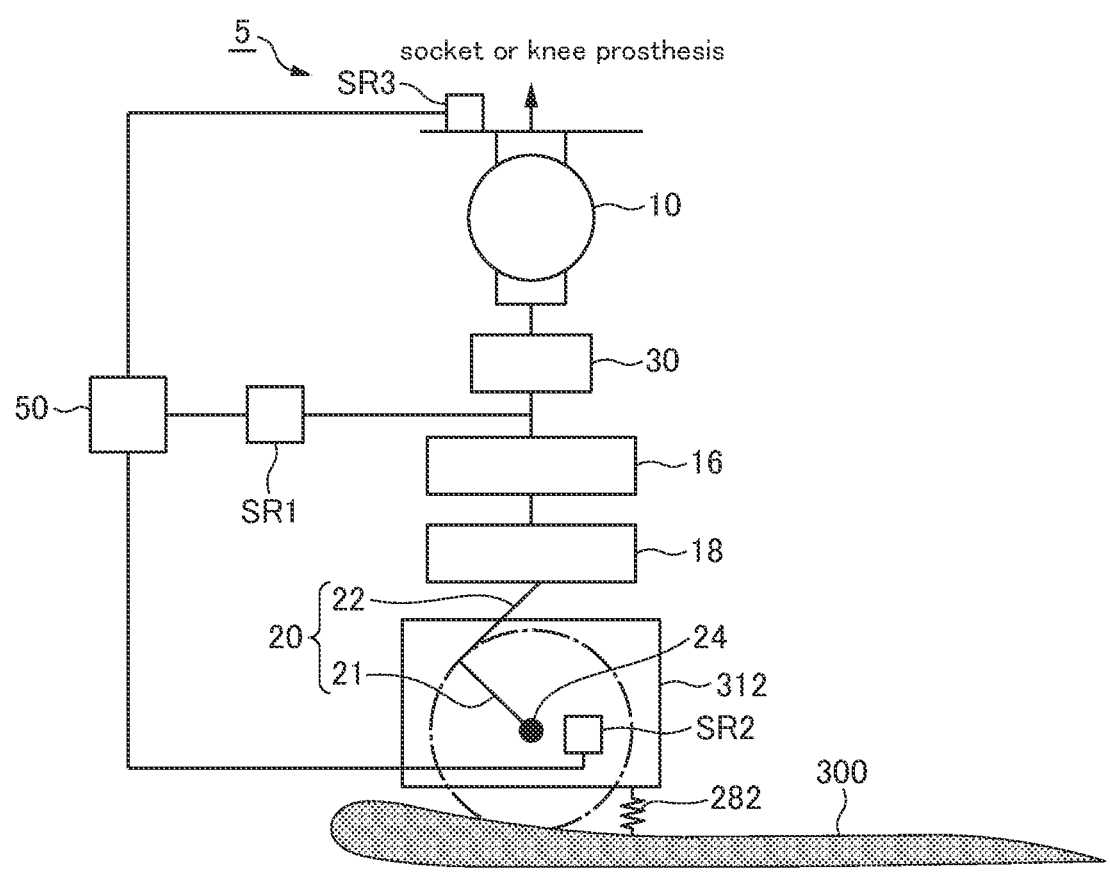
FIG. 30 is an example of a block diagram showing a Modification Example of the assistance device according to the third embodiment of the present invention.

FIG. 30 is an example of a block diagram showing a Modification Example of the present embodiment. The assistance device 5 shown in the figure includes a parallel spring 282 that is arranged between the ankle part 24 and the foot part 300, more specifically, between the joint frame 312 and the foot part 300 and is mounted in parallel with the slider crank 20. The other configurations of the assistance device 5 of this Modification Example are substantially the same as those of the assistance device 1 shown in FIG. 4.

The material of the parallel spring 282 may be the same as the parallel spring 281, the plantar flexion spring 181 and the dorsal flexion spring 182, or may be a material having more excellent compressive/repulsive force.

By arranging the parallel spring 282 at such a position, as in the case of the assistance device 4 shown in FIG. 29, further energizing force can be obtained during the walking operation, and smoother and safer walking becomes possible. Since the load of the motor is also reduced correspondingly by the additional energizing force by the parallel spring, it is possible to realize further energy efficiency and device weight reduction.

In this embodiment, the parallel springs 281 and 282 correspond to, for example, "the first parallel spring" and "the second parallel spring", respectively, and both correspond to, for example, "the second elastic member". It is to be noted that the series springs 181 and 182 in the cylinder 90 correspond to, for example, "the first elastic member".

In the present embodiment, a mode in which the parallel spring 281 or 282 is added to the configuration of the first embodiment has been described in order to contribute to easy understanding, but the present invention is not limited to this, and for example, the parallel springs 281 or 282 can be similarly added to the configurations of the assistance device 2 of the Modification Example and the assistance device 3 of the second embodiment.

Here, it is to be noted that the assistance device according to the present invention is not limited to the case where only the series springs 181 and 182 (the above-described assistance devices 1 to 3) are provided, and the case where the series springs 181 and 182 and the parallel spring 281 or the parallel spring 282 (the assistance devices 4 and 5 of the present embodiment) are provided, but can be used, in accordance with the required specification, even in when one of the parallel springs 281 and 282 is only provided or even when none of the series springs 181 and 182 and the parallel springs 281 and 282 is provided.

(4) Comparative Experiments

The difference in characteristics due to the presence/absence of the elastic part and the presence/absence of the brake is subjected to a Comparative experiment. Hereinafter, description will be given with reference to the drawings.

(a) Presence/Absence of Elastic Part

Figure 31A:
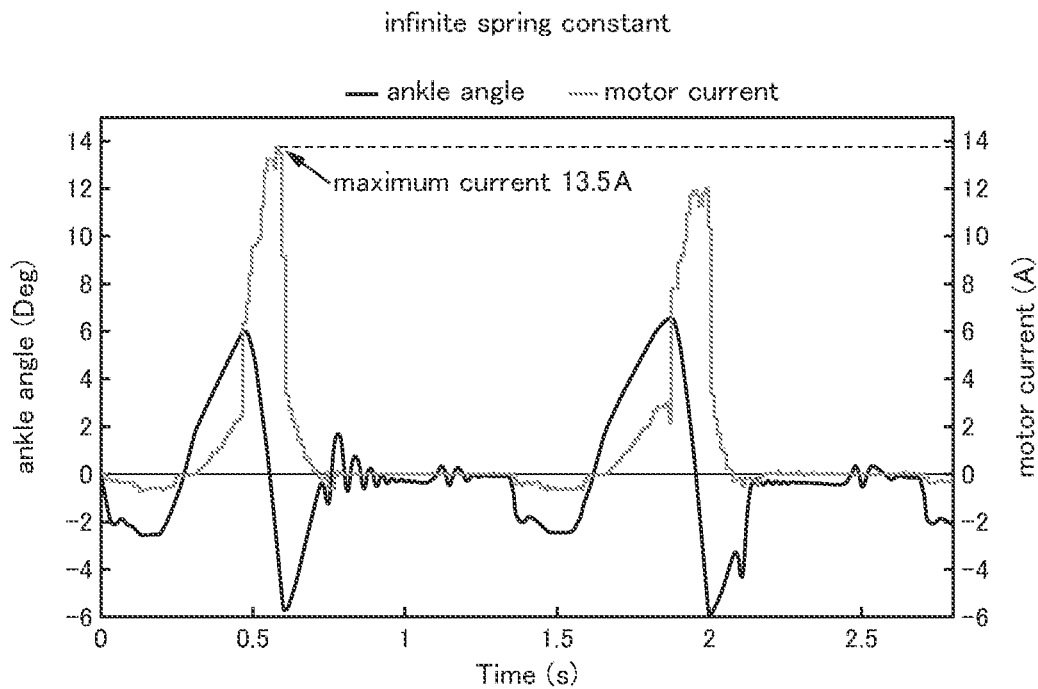
FIG. 31A is an example of a graph showing the results of an Experimental Example performed to compare the difference in characteristics with and without an elastic part.
Figure 31B:
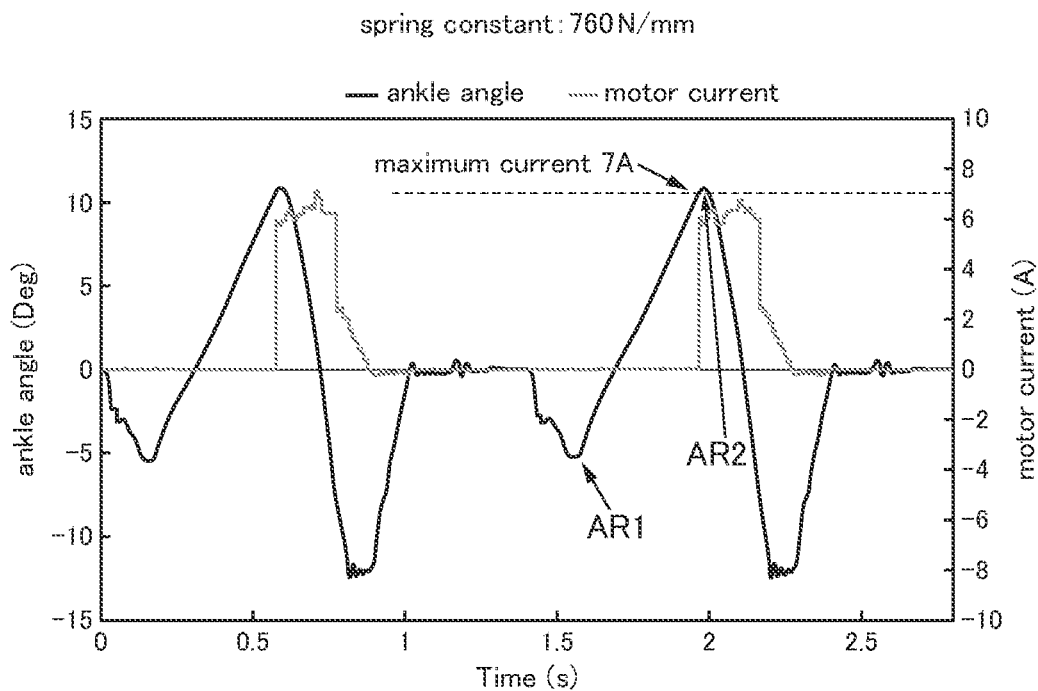
FIG. 31B is an example of a graph showing the results of an Experimental Example performed to compare the difference in characteristics with and without an elastic part.

A characteristic comparison between the case where the elastic part is provided in the above-described embodiment and the case where an aluminum pipe having an infinite spring constant is used instead of the elastic part is obtained by an experiment of walking on a treadmill at 3.5 km/h. As a characteristic, the maximum current amount and the ankle angle are taken up and recorded FIG. 31A shows an experimental result by an example of an assistance device using an aluminum pipe instead of an elastic part such as a spring, and FIG. 31B shows an example of an assistance device using an elastic part having a spring constant of 760 N/mm.

As is clear from the comparison of both figures, it can be seen that the maximum current value was significantly improved from 13.5 A to 7 A by changing the aluminum pipe to the elastic part having a spring constant of 760 N/mm due to the effect of energy accumulation and release by the elastic element. Furthermore, It can be seen that, as shown by arrows AR1 and AR2 in FIG. 31B, in this experimental example including an elastic part, the impact from the object is absorbed at the plantar flexion of about 5°, and the energy is accumulated in the elastic part at the dorsal flexion of about 11 degrees.

(b) Presence/Absence of Brake

Figure 32A:
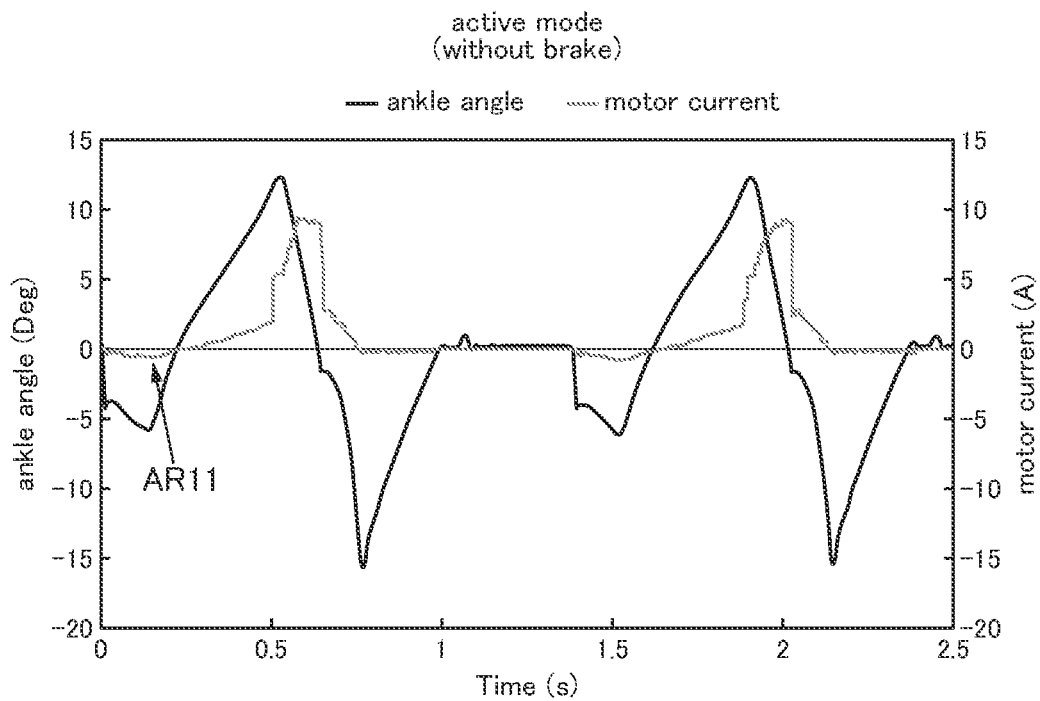
FIG. 32A is an example of a graph showing the results of an Experimental Example performed to compare the difference in characteristics with and without a brake.
Figure 32B:
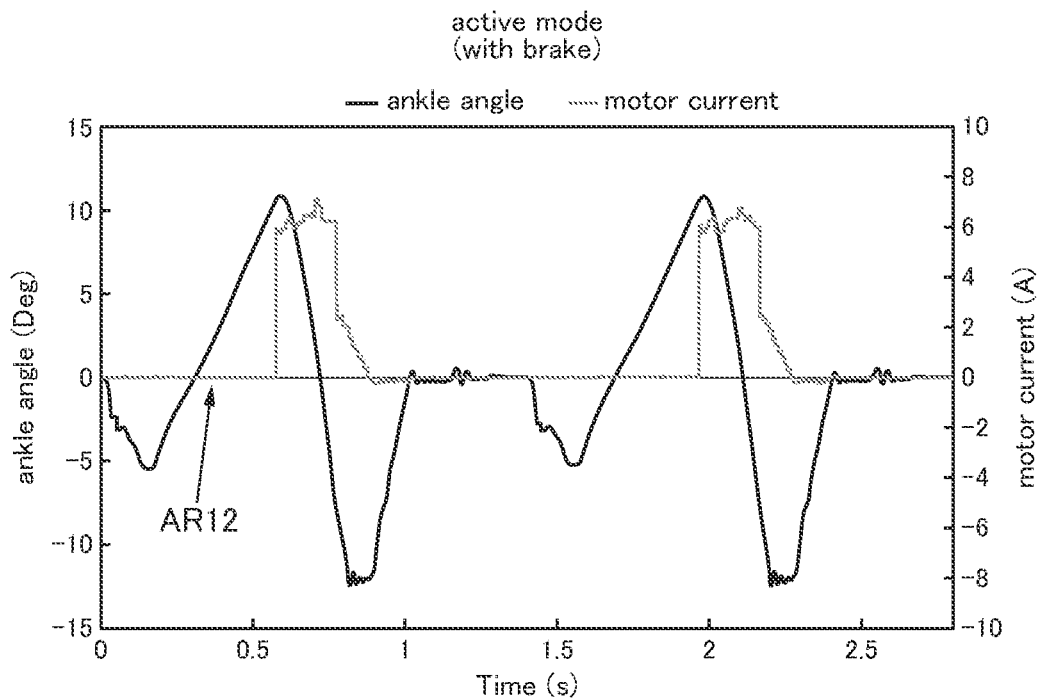
FIG. 32B is an example of a graph showing the results of an Experimental Example performed to compare the difference in characteristics with and without a brake.
Figure 32C:
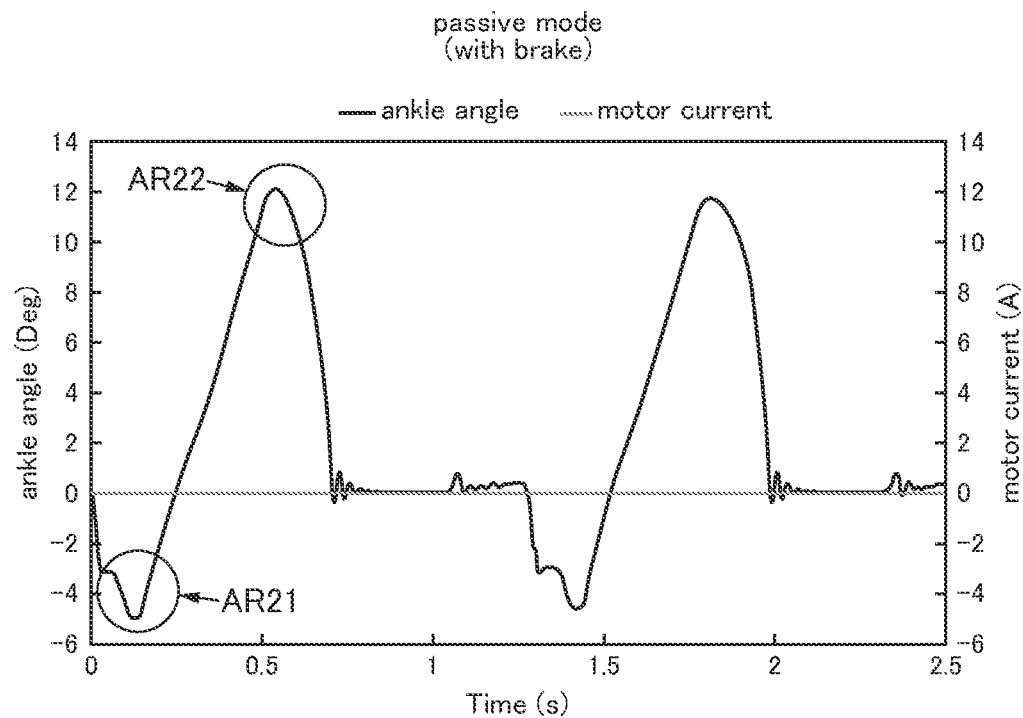
FIG. 32C is another example of a graph showing the results of an Experimental Example performed to compare the difference in characteristics with and without a brake.

Results of an experimental example for verifying the change in current characteristics according to the presence/absence of a brake in the embodiment of the assistance device according to the present invention are shown in FIG. 32A to FIG. 32C. FIG. 32A and FIG. 32B show a variation example of the current characteristics according to the presence/absence of a brake in the active mode, and FIG. 32C shows an example of the current characteristics in the passive mode when a brake is present.

As is clear from the comparison between FIG. 32A and FIG. 32B, when there is no brake, it is necessary to extract the holding force from the motor, so that energy consumption occurs even in the stance phase (see arrow AR11).

On the other hand, when the assistance device includes a brake, the holding force is obtained from the brake, so the motor does not operate in the stance phase (see arrow AR12). Therefore, there is an advantage that energy consumption is not generated in the stance phase and the energy efficiency is correspondingly improved.

Furthermore, as shown in FIG. 32C, even in the passive mode, when the assistance device includes a brake, due to the holding force obtained from the brake, plantar flexion of about 5° (arrow AR21) and dorsal flexion of about 11° (arrow AR22) are realized in the stance phase by the bending of the elastic part caused by its self-gravity. This means that even if the battery runs out during use, switching to the passive type allows continued use without any problems. Thus, even in the active type artificial foot, by providing a brake, it is possible to use the artificial foot at any time by switching the mode from the active type to the passive type, so that an assistance device including a hybrid artificial foot with extremely high practicality is provided.

(5) Power Suit

Figure 33A:
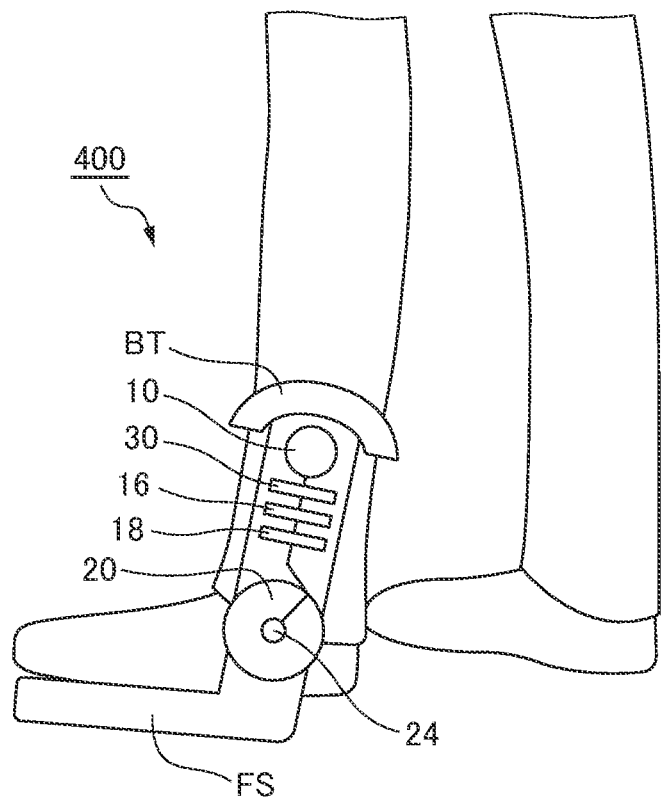
FIG. 33A is an example of a schematic side view showing an example of a power suit using an embodiment of the assistance device according to the present invention.
Figure 33B:
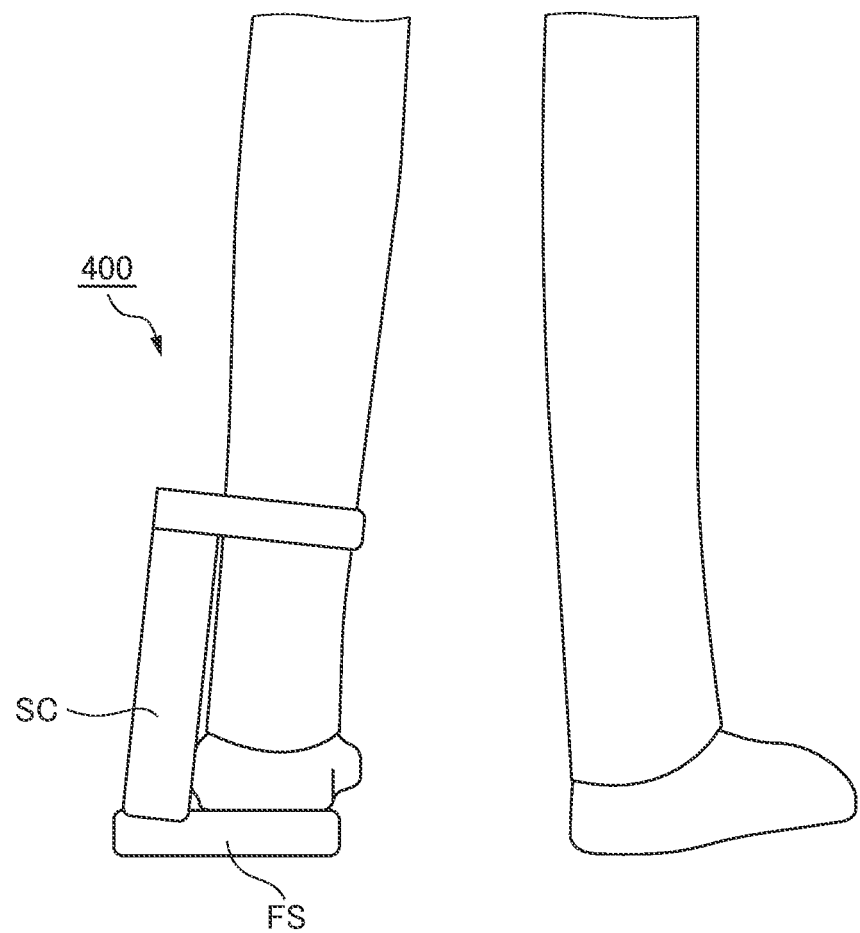
FIG. 33B is an example of a schematic rear view showing an example of a power suit using an embodiment of the assistance device according to the present invention.

An example of a power suit using the embodiment of the assistance device according to the present invention is shown in FIG. 33A and FIG. 33B. The power suit 400 of this example is realized by using the assistance device 1 according to the embodiment shown in FIG. 4. The power suit 400 include: a suit cover SC that covers and protects the assistance device 1; a foot support FS having a size capable of supporting the assistance device 1 and carrying the user's shoe on the top surface; and a belt BT for fixing the power suit 400 to the user's ankle, in addition to the assistance device 1 including a motor 10, a brake 30, a transmission mechanism 16, an elastic part 18, a slider crank 20 and an ankle part 24. Incidentally, for easy understanding of the device configuration, depiction of the suit cover SC is omitted in the side view of FIG. 33A.

Thus, according to this example, since the assistance device of the above-described embodiment is used, a lightweight and highly practical power suit with excellent energy efficiency is provided.

In this example, an example in which the assistance device 1 shown in FIG. 4 is used is shown, but the present invention is not limited to this, and the power suit can be configured by using the assistance device according to any of the other embodiments.

Although the embodiments of the assistance device and the assistance method according to the present invention have been described above, the present invention is not limited to these embodiments, and various improvements and modifications can be used. For example, in the above embodiment, the case where the assistance device according to the present invention is applied to an artificial foot has been described as an example, but the present invention is not limited to this. As long as there is one that performs joint motion of the assistance target, it can also be used by attaching it to, for example, an artificial hand in addition to the artificial foot. In that case, for example, a wall or stairs corresponds to an "object", and the on/off of the braking part is controlled by using the abutting/pushing out with respect to them as a management parameter.

Furthermore, in the above embodiment, the case where the braking part such as the brake 30 and the route switching part 54 is provided has been described, but the present invention is not limited to this. For example, even if a braking part is not provided and even if only a sensor such as the inertia measuring sensor SR1, the angle sensor SR2 and the force sensor SR3, and a controlling part that processes a detection signal from these sensors are provided, contact/non-contact of the movable part with respect to the object and the movement stage during contact can be estimated, so it is possible to sufficiently contribute to facilitating the motion of the wearer by feeding back the estimated information to the wearer.

Moreover, it is to be noted that the braking part, the above sensor and control part, and the elastic part are not essential components, and even when these components are not provided, it is fully possible to realize safe walking, high energy efficiency, and weight reduction of the device simply by providing a motor, a driving part, and a crank mechanism provided between the driving part and the foot part.

EXPLANATION OF REFERENCE SYMBOLS 1,2,3,4,5 . . . assistance device,
10,200 . . . motor,
16 . . . transmission mechanism,
18 . . . (first) elastic member,
20 . . . slider crank (crank mechanism),
24 . . . ankle part,
30 . . . brake,
50 . . . controller,
54 . . . route switching part,
60 . . . battery,
70 . . . ball screw,
90 . . . cylinder,
181 . . . plantar flexion spring,
182 . . . dorsal flexion spring,
281 . . . parallel spring (second elastic member, first parallel spring),
281 . . . parallel spring (second elastic member, second parallel spring),
310,312 . . . joint frame
400 . . . power suit,
501 . . . IMU sensor (inertia measuring sensor),
502 . . . absolute encoder (angle sensor),
BT . . . belt,
FS . . . foot support,
SR1 . . . inertia measuring sensor,
SR2 . . . angle sensor,
SR3 . . . force sensor,
R . . . resistor,
SC . . . suit cover,
SW1, SW2 . . . switch.

What is claimed is:

1. An assistance device to assist a joint motion of a foot part, the device comprising:
   a driving part which comprises a motor and a transmission mechanism to change a speed of the motor, and converts a rotational motion of the motor into a linear motion;
   an elastic part which alleviates an impact from an object through the foot part and accumulates an impact force or self-gravity by compression, and releases an accumulated energy by stretching to apply an energizing force for motion assistance; and
   a crank mechanism which is provided between the driving part and the foot part, and an ankle part connected to the crank mechanism, the ankle part comprising a rotation shaft,
   wherein:
   the crank mechanism comprises a crank connected to and rotatable around the rotation shaft of the ankle part, and a rod with one end and the other end, the one end of the rod being connected to a leading end of the driving part, the other end of the rod being connected to the crank, and wherein:
   the crank mechanism is constituted so as to make one end of the rod on the side opposite to the driving part side to perform circulation motion, make the crank rotate around the rotation shaft of the ankle part, converts the linear motion into a rotational motion while changing a deceleration ratio by the crank, thereby transmitting the rotational motion to the foot part via the ankle part, the deceleration ratio rate is expressed by a following expression:

$$K\frac{2\pi NbR}{2LbNm}$$

Nm is a number of teeth of a pulley on a side of motor in the transmission mechanism, Nb is a number of teeth of the pulley on a side of a ball screw in the transmission mechanism, Lb is a lead length of the ball screw, R is a arm length of the ankle part, and K is a deceleration coefficient by the crank represented as follows:

$$K = \frac{\text{Sin}(\alpha + \beta)}{\text{Cos}\beta}$$

wherein α is an angle between an arm of the ankle part and a vertical direction, and β is an angle between the vertical direction and the rod.

2. The assistance device according to claim 1, further comprising a control part which adjusts torque of the motor by estimating a moving situation of a user within a walking cycle and controlling the driving part according to an estimated moving situation.

3. The assistance device according to claim 2, further comprising a sensor which detects a relationship between the assistance device and the object and outputs a signal, wherein the control part analyzes the signal from the sensor and estimates the moving situation.

4. The assistance device according to claim 3, further comprising a braking part to brake the motion of the driving part, wherein the sensor comprises:

a first sensor to detect an angular velocity and an acceleration;

a second sensor to detect a rotation angle of the movable part; and a third sensor to detect a repulsive force from the object, the control part controls the braking part based on signals from the first sensor to the third sensor.

5. The assistance device according to claim 4, wherein the relationship between the assistance device and the object includes a positional relationship, the control part estimates from the signal of the third sensor whether the movable part is in a first phase of contacting with the object, or in a second phase of being separated from the object, turns on the braking of the braking part when the movable part is estimated to be in the second phase and when the rotation angle becomes 0° by a signal from the second sensor, and turns off the braking of the braking part when first to third values obtained by processing signals from the first to third sensors exceed a predetermined reference value.

6. The assistance device according to claim 4, wherein the braking part includes a brake attached to at least one end of both ends of rotation shaft of the motor.

7. The assistance device according to claim 4, wherein the braking part comprises a switching part to perform switching between a current supply to the motor and a short circuit of the motor, and reduces the rotational speed of the motor by converting rotational energy into electric energy by a short circuit of the motor.

8. The assistance device according to claim 4, comprising an hybrid artificial foot with two modes of an active type and a passive type, wherein the hybrid artificial foot comprises the braking part, so that constant use is enabled by switching the mode from the active type to the passive type when a battery runs out during use.

9. The assistance device according to claim 1, wherein the elastic part comprises at least any of:

a first elastic member provided between the transmission mechanism and the crank mechanism; and a second elastic member provided between the driving part and the foot part in parallel with the crank mechanism.

10. The assistance device according to claim 9, wherein the second elastic member comprises at least any of: a first parallel spring provided between the driving part and the ankle part; and a second parallel spring provided between the ankle part and the foot part.

11. A control method of an assistance device to assist a joint motion of a lower limb, wherein the assistance device comprises:

a driving part which comprises a motor and a transmission mechanism to change a speed of the motor, and converts a rotational motion of the motor into a linear motion;

an elastic part which alleviates an impact from an object through a foot part and accumulates an impact force by compression, and releases an accumulated energy by stretching to apply an energizing force for motion assistance; and a crank mechanism which is provided between the driving part and the foot part, and converts the linear motion into a rotational motion while changing a deceleration ratio, thereby transmitting the rotational motion to the foot part via an ankle part, the crank mechanism comprises a crank connected to and rotatable around the rotation shaft of the ankle part, and a rod with one end and the other end, the one end of the rod being connected to a leading end of the driving part, the other end of the rod being connected to the crank, the deceleration ratio rate is expressed by a following expression:

$$K\frac{2\pi NbR}{2LbNm}$$

Nm is a number of teeth of a pulley on a side of motor in the transmission mechanism, Nb is a number of teeth of the pulley on a side of a ball screw in the transmission mechanism, Lb is a lead length of the ball screw, R is a arm length of the ankle part, and K is a deceleration coefficient by the crank represented as follows:

$$K = \frac{\text{Sin}(\alpha + \beta)}{\text{Cos}\beta}$$

wherein "α" is an angle between an arm of the movable part and a vertical direction, and "β" is an angle between the vertical direction and the rod,
and wherein:
walking can be assisted by accumulating and releasing energy by the elastic part in addition to adjusting torque of the motor by estimating moving situation of a user within a walking cycle and controlling the driving part according to an estimated moving situation.

* * * * *